US011905313B2

(12) United States Patent
Khurana

(10) Patent No.: US 11,905,313 B2
(45) Date of Patent: Feb. 20, 2024

(54) RECOMBINANT RSV G PROTEINS AND THEIR USE

(71) Applicant: The United States of America, as represented by the Secretary, Department of Health and Human Services, Silver Spring, MD (US)

(72) Inventor: Surender Khurana, Clarksburg, MD (US)

(73) Assignee: The United States of America, as represented by the Secretary, Department of Health and Human Services., Silver Spring, MD (US)

( * ) Notice: Subject to any disclaimer, the term of this patent is extended or adjusted under 35 U.S.C. 154(b) by 770 days.

(21) Appl. No.: 16/763,497

(22) PCT Filed: Nov. 27, 2018

(86) PCT No.: PCT/US2018/062623
§ 371 (c)(1),
(2) Date: May 12, 2020

(87) PCT Pub. No.: WO2019/108541
PCT Pub. Date: Jun. 6, 2019

(65) Prior Publication Data
US 2020/0299335 A1 Sep. 24, 2020

Related U.S. Application Data

(60) Provisional application No. 62/591,533, filed on Nov. 28, 2017.

(51) Int. Cl.
| | | |
|---|---|---|
| *C07K 14/005* | (2006.01) | |
| *A61P 31/14* | (2006.01) | |
| *A61K 39/155* | (2006.01) | |
| *C07K 7/06* | (2006.01) | |
| *G01N 33/569* | (2006.01) | |
| *A61K 39/00* | (2006.01) | |

(52) U.S. Cl.
CPC .......... *C07K 14/005* (2013.01); *A61K 39/155* (2013.01); *A61P 31/14* (2018.01); *C07K 7/06* (2013.01); *G01N 33/56983* (2013.01); *A61K 2039/5258* (2013.01); *A61K 2039/53* (2013.01); *C07K 2319/03* (2013.01); *C12N 2760/18522* (2013.01); *C12N 2760/18523* (2013.01); *G01N 2333/135* (2013.01)

(58) Field of Classification Search
None
See application file for complete search history.

(56) References Cited

U.S. PATENT DOCUMENTS

| | | | |
|---|---|---|---|
| 7,666,433 B2 | 2/2010 | Hancock et al. | |
| 10,000,553 B2 * | 6/2018 | Coyle | A61P 27/02 |
| 2008/0233150 A1 * | 9/2008 | Smith | A61K 39/155 |
| | | | 530/387.3 |

FOREIGN PATENT DOCUMENTS

| | | |
|---|---|---|
| WO | WO 2008/114149 A2 | 9/2008 |
| WO | WO 2013/116965 A1 | 8/2013 |
| WO | WO 2015/084838 A1 | 6/2015 |

OTHER PUBLICATIONS

Teng et al., Journal of Virology, p. 6164-6171vol. 76, No. 12 (Year: 2002).*
Laria et al., Vaccine vol. 32, pp. 1072-1078 (Year: 2014).*
Agoti et al., "Genetic Relatedness of Infecting and Reinfecting Respiratory Syncytial Virus Strains Identified in a Birth Cohort from Rural Kenya," *J Infect Dis.* 206: 1532-1541, Nov. 2012.
Anderson et al., "Neutralization of Respiratory Syncytial Virus by Individual and Mixtures of F and G Protein Monoclonal Antibodies," *J Virol.* 62.11: 4232-4238, Nov. 1988.
Boyoglu-Barnum et al., "Mutating the CX3C Motif in the G Protein Should Make a Live Respiratory Syncytial Virus Vaccine Safer and More Effective," *J Virol.* 91.10: e02059-16, May 2017 (17pages).
Cane and Pringle, "Evolution of Subgroup A Respiratory Syncytial Virus: Evidence for Progressive Accumulation of Amino Acid Changes in the Attachment Protein," *J Virol.* 69.5: 2918-2925, May 1995.
Capella et al., "Prefusion F, Postfusion F, G Antibodies, and Disease Severity in Infants and Young Children with Acute Respiratory Syncytial Virus Infection," *J Infect Dis.* 216: 1398-1406, Dec. 2017.
Collarini et al., "Potent High-Affinity Antibodies for Treatment and Prophylaxis of Respiratory Syncytial Virus Derived from B Cells of Infected Patients," *J Immunol.* 183.10: 6338-6345, Oct. 2009.
Collins and Melero, "Progress in Understanding and Controlling Respiratory Syncytial Virus: Still Crazy After All These Years," *Virus Res.* 162.1-2: 80-99, Dec. 2011.
Cortjens et al., "Broadly Reactive Anti-Respiratory Syncytial Virus G Antibodies from Exposed Individuals Effectively Inhibit Infection of Primary Airway Epithelial Cells," *J Virol.* 91.10: e02357-16, May 2017 (15 pages).
Fuentes et al., "Development of a Simple, Rapid, Sensitive, High-Throughput Luciferase Reporter Based Microneutralization Test for Measurement of Virus Neutralizing Antibodies Following Respiratory Syncytial Virus Vaccination and Infection," *Vaccine* 31.37: 3987-3994, Aug. 2013.

(Continued)

Primary Examiner — Shanon A. Foley
Assistant Examiner — Myron G Hill
(74) Attorney, Agent, or Firm — Klarquist Sparkman, LLP

(57) ABSTRACT

Embodiments of a recombinant Respiratory Syncytial Virus (RSV) G ectodomain are provided. Also disclosed are nucleic acids encoding the RSV G ectodomain and methods of producing the RSV G ectodomain. Methods for inducing an immune response in a subject are also disclosed. In some embodiments, the method can be a method for inhibiting a RSV infection in a subject by administering an effective amount of the recombinant RSV G ectodomain to the subject to produce a protective immune response.

28 Claims, 14 Drawing Sheets

Specification includes a Sequence Listing.

(56) References Cited

OTHER PUBLICATIONS

Fuentes et al., "Nonglycosylated G-Protein Vaccine Protects Against Homologous and Heterologous Respiratory Syncytial Virus (RSV) Challenge, while Glycosylated G Enhances RSV Lung Pathology and Cytokine Levels," *J Virol.* 89.16: 8193-8205, Aug. 2015.

Fuentes et al., "Antigenic Fingerprinting following Primary RSV Infection in Young Children Identifies Novel Antigenic Sites and Reveals Unlinked Evolution of Human Antibody Repertoires to Fusion and Attachment Glycoproteins," *PLoS Pathogens* 12.4: e1005554, Apr. 2016 (30 pages).

Fuentes et al., "Development of Bioluminescence Imaging of Respiratory Syncytial Virus (RSV) in Virus-Infected Live Mice and Its Use for Evaluation of Therapeutics and Vaccines," *Vaccine* 35.4: 694-702, Jan. 2017.

Fuentes et al., "Preclinical Evaluation of Bacterially Produced RSV-G Protein Vaccine: Strong Protection Against RSV Challenge in Cotton Rat Model," *Sci Rep.* 7: 42428, Feb. 2017 (13 pages).

Hall, "Respiratory Syncytial Virus and Parainfluenza Virus," *N Engl J Med.* 344.25: 1917-1928, Jun. 2001.

Haynes et al., "Therapeutic Monoclonal Antibody Treatment Targeting Respiratory Syncytial Virus (RSV) G Protein Mediates Viral Clearance and Reduces the Pathogenesis of RSV Infection in BALB/c Mice, " *J Infect Dis.* 200: 439-447, Aug. 2009.

Heidema et al., "Human CD8+ T Cell Responses Against Five Newly Identified Respiratory Syncytial Virus-Derived Epitopes," *J Gen Virol.* 85: 2365-2374, 2004.

Imai and Yasuda, "Therapeutic Intervention of Inflammatory/Immune Diseases by Inhibition of the Fractalkine (CX3CL1)-CX3CR1 Pathway," *Inflamm Regen.* 36: 9, Jun. 2016 (5 pages).

Jeong et al., "CX3CR1 is Expressed in Differentiated Human Ciliated Airway Cells and Co-Localizes with Respiratory Syncytial Virus on Cilia in a G Protein-Dependent Manner," *PLoS One* 10.6: e0130517, Jun. 2015 (13 pages).

Johnson et al., "Respiratory Syncytial Virus Uses CX3CR1 as a Receptor on Primary Human Airway Epithelial Cultures, " *PLoS Pathogens* 11.12: e1005318, Dec. 2015 (16 pages).

Jones et al., "Structural Basis for Recognition of the Central Conserved Region of RSV G by Neutralizing Human Antibodies," *PLoS Pathogens* 14.3: e1006935, Mar. 2018 (23 pages).

Lee et al., "Protective Antigenic Sites in Respiratory Syncytial Virus G Attachment Protein Outside the Central Conserved and Cysteine Noose Domains," *PLoS Pathogens* 14.8: e1007262, Aug. 2018 (22 pages).

Melero et al., "Structural, Antigenic and Immunogenic Features of Respiratory Syncytial Virus Glycoproteins Relevant for Vaccine Development," *Vaccine* 35.3: 461-468, Jan. 2017.

Mufson et al., "Two Distinct Subtypes of Human Respiratory Syncytial Virus," *J Gen Virol.* 66: 2111-2124, 1985.

Nair et al., "Global Burden of Acute Lower Respiratory Infections Due to Respiratory Syncytial Virus in Young Children: A Systematic Review and Meta-Analysis," *Lancet* 375.9725: 1545-1555, May 2010.

Nicholas et al., "Cytolytic L-Lymphocyte Responses to Respiratory Syncytial Virus: Effector Cell Phenotype and Target Proteins," *J Virol.* 64.9: 4232-4241, Sep. 1990.

Openshaw and Tregoning, "Immune Responses and Disease Enhancement during Respiratory Syncytial Virus Infection," *Clin Microbiol Rev.* 18.3: 541-555, Jul. 2005.

Power et al., "The Immunogenicity, Protective Efficacy and Safety of BBG2Na, a Subunit Respiratory Syncytial Virus (RSV) Vaccine Candidate, Against RSV-B," *Vaccine* 22.2: 168-176, Dec. 2003.

Sparer et al., "Eliminating a Region of Respiratory Syncytial Virus Attachment Protein Allows Induction of Protective Immunity without Vaccine-Enhanced Lung Eosinophilia," *J Exp Med.* 187.11: 1921-1926, Jun. 1998.

Tan et al., "Genetic Variability Among Complete Human Respiratory Syncytial Virus Subgroup A Genomes: Bridging Molecular Evolutionary Dynamics and Epidemiology," *PLoS One* 7.12: e51439, Dec. 2012 (15 pages).

Tebbey et al., "Atypical Pulmonary Eosinophilia is Mediated by a Specific Amino Acid Sequence of the Attachment (G) Protein of Respiratory Syncytial Virus," *J Exp Med.* 188.10: 1967-1972, Nov. 1998.

Tripp et al., "CX3C Chemokine Mimicry by Respiratory Syncytial Virus G Glycoprotein," *Nat Immunol.* 2.8: 732-738, Aug. 2001.

Tripp et al., "Respiratory Syncytial Virus: Targeting the G Protein Provides a New Approach for an Old Problem," *J Virol.* 92.3: e01302-17, Feb. 2018 (8 pages).

Zhivaki et al., "Respiratory Syncytial Virus Infects Regulatory B Cells in Human Neonates via Chemokine Receptor CX3CR1 and Promotes Lung Disease Severity," *Immunity* 46: 301-314, Feb. 2017.

\* cited by examiner

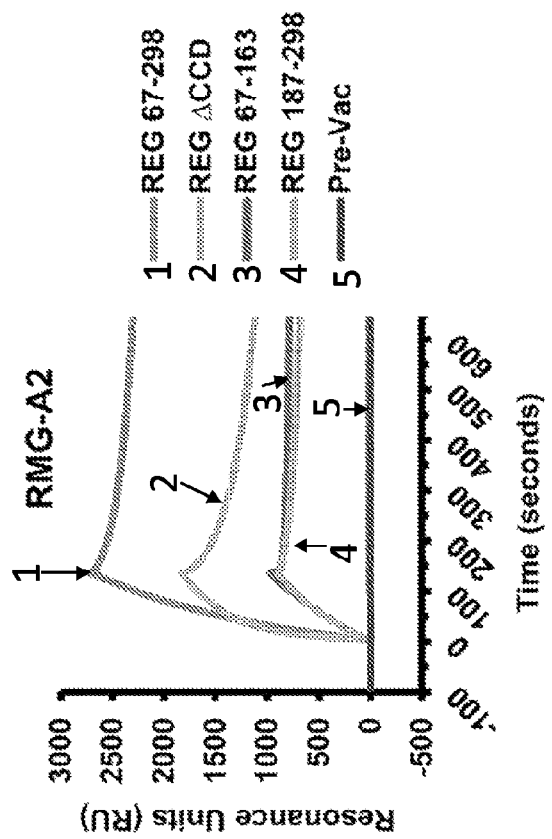

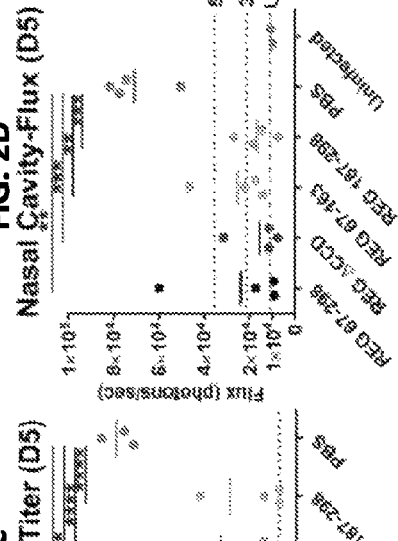
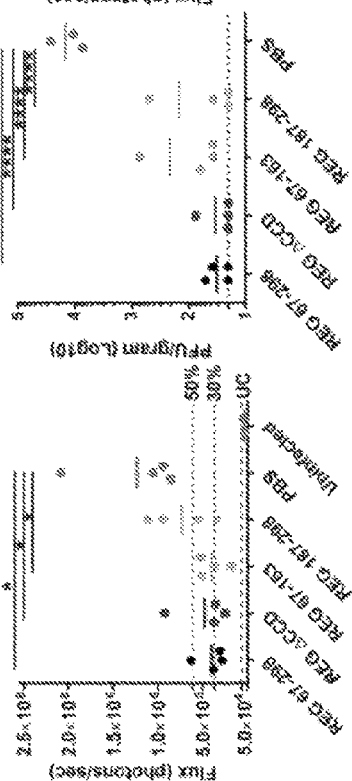
FIG. 2A, FIG. 2B, FIG. 2C, FIG. 2D

ELISA (A2)

ELISA (B1)

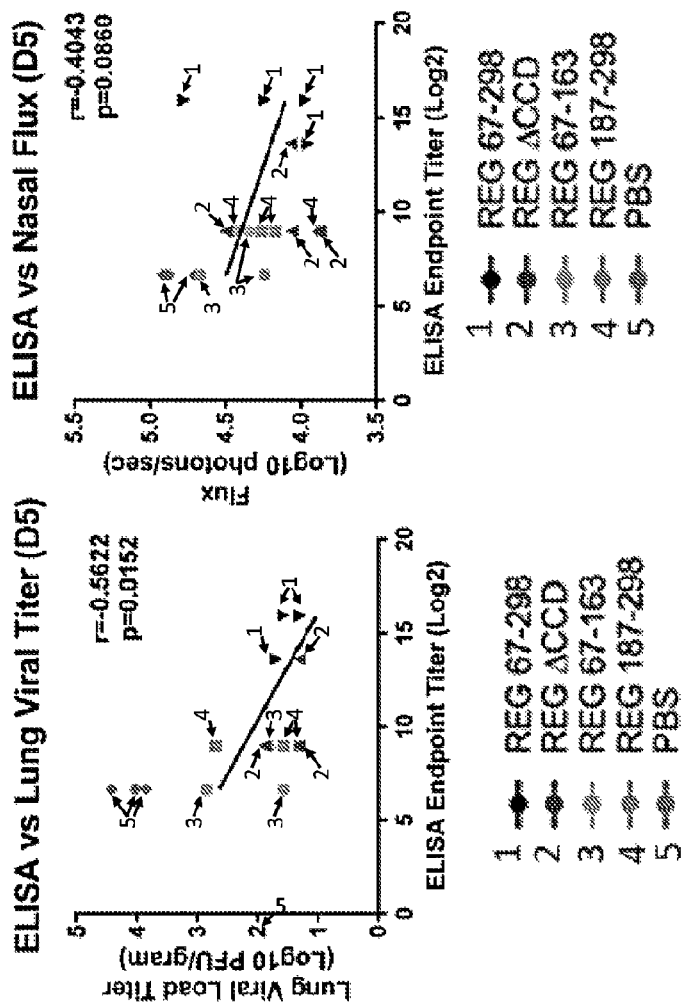
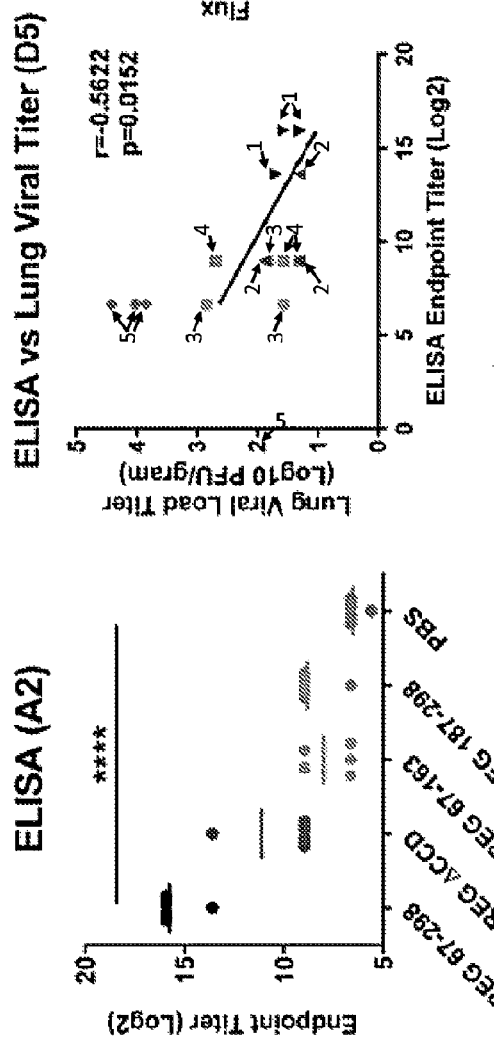

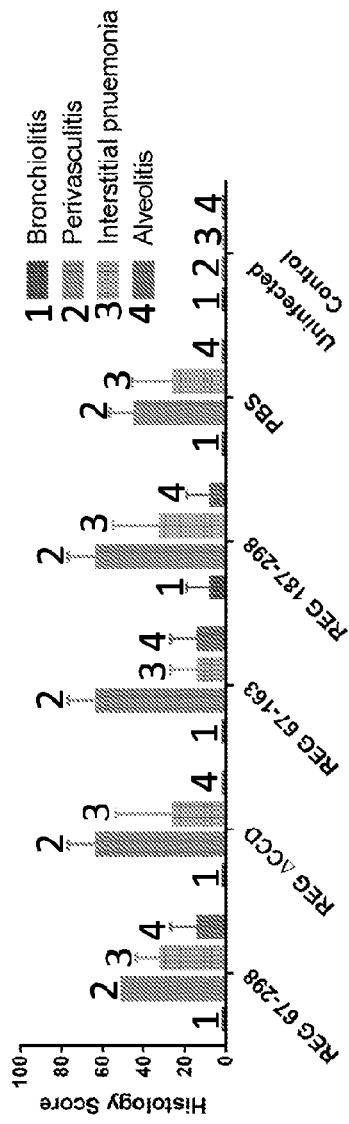
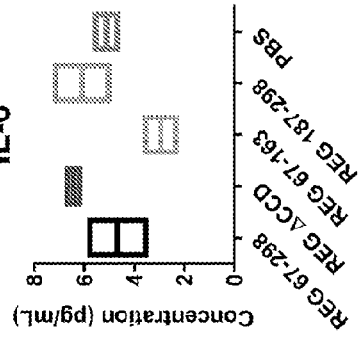
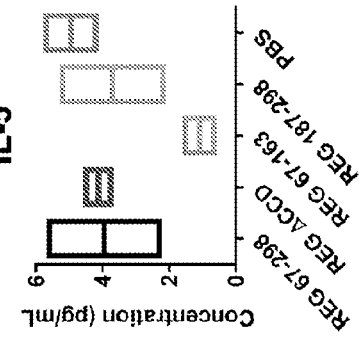
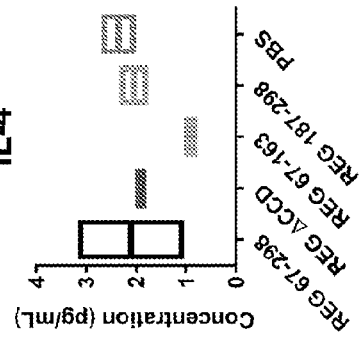

IL-13

IFN-γ

Eotaxin

MCP-1

MIP-1α

Th2/Th1 ratio

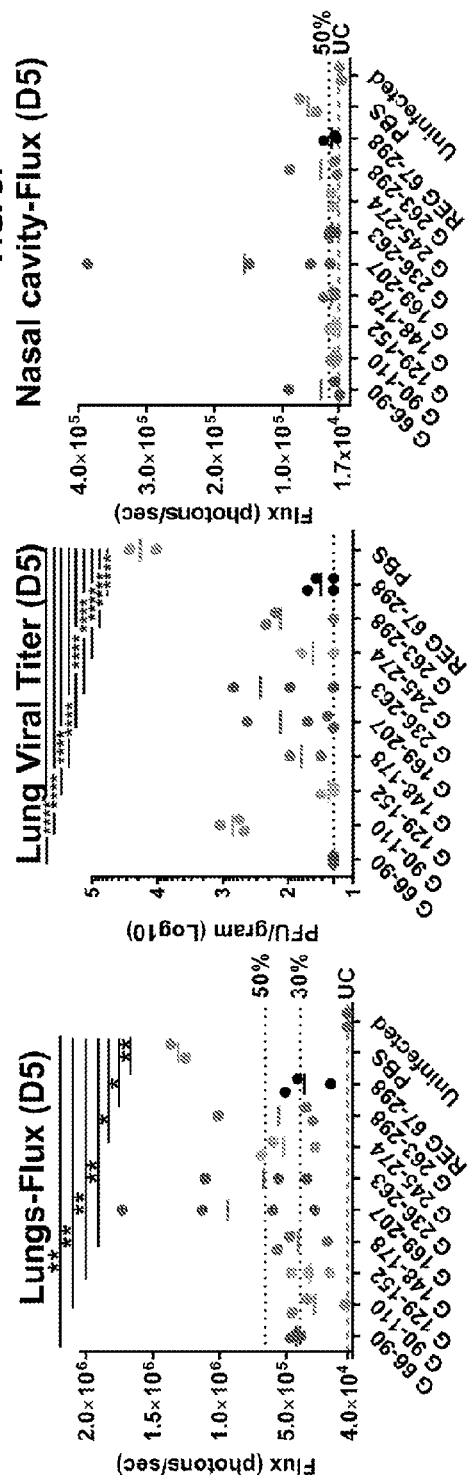

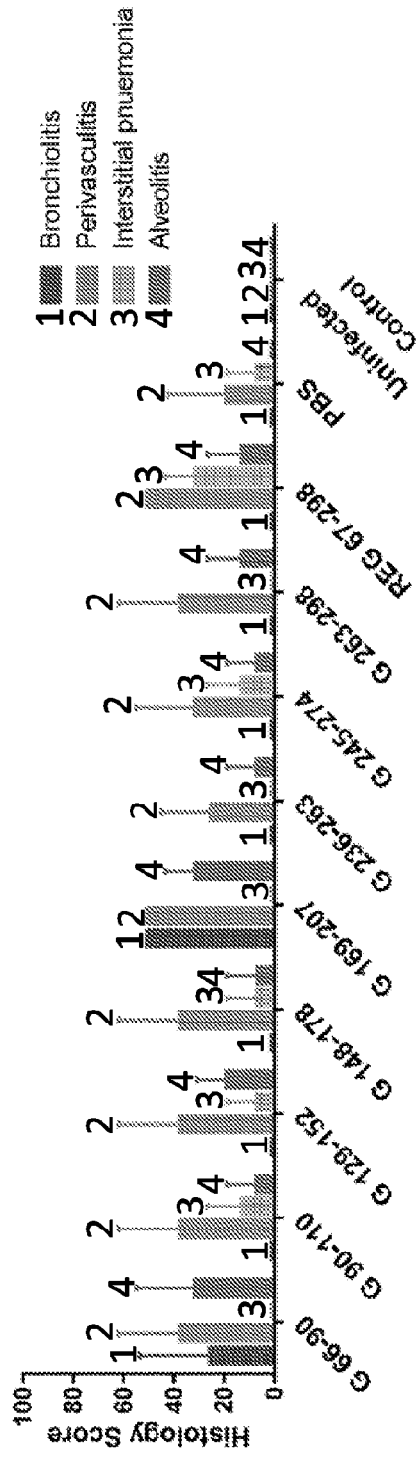
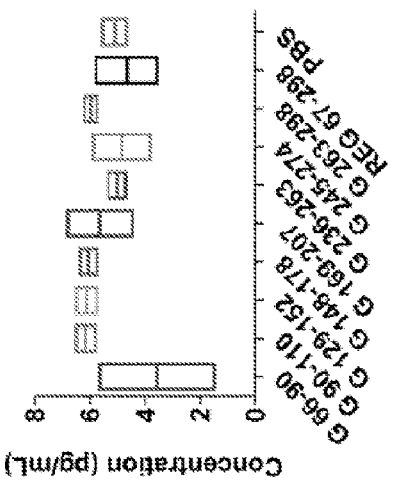
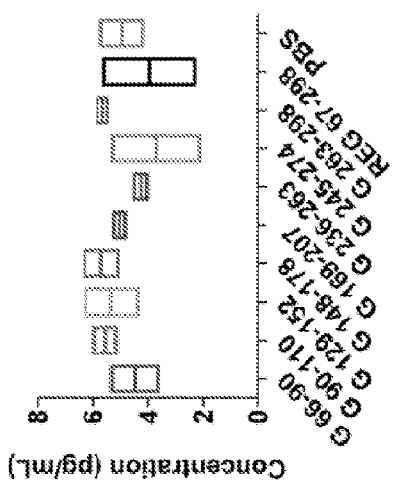
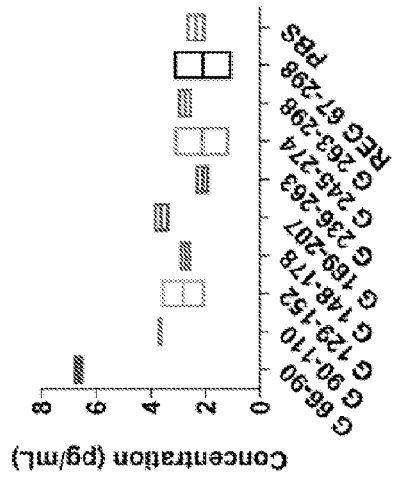

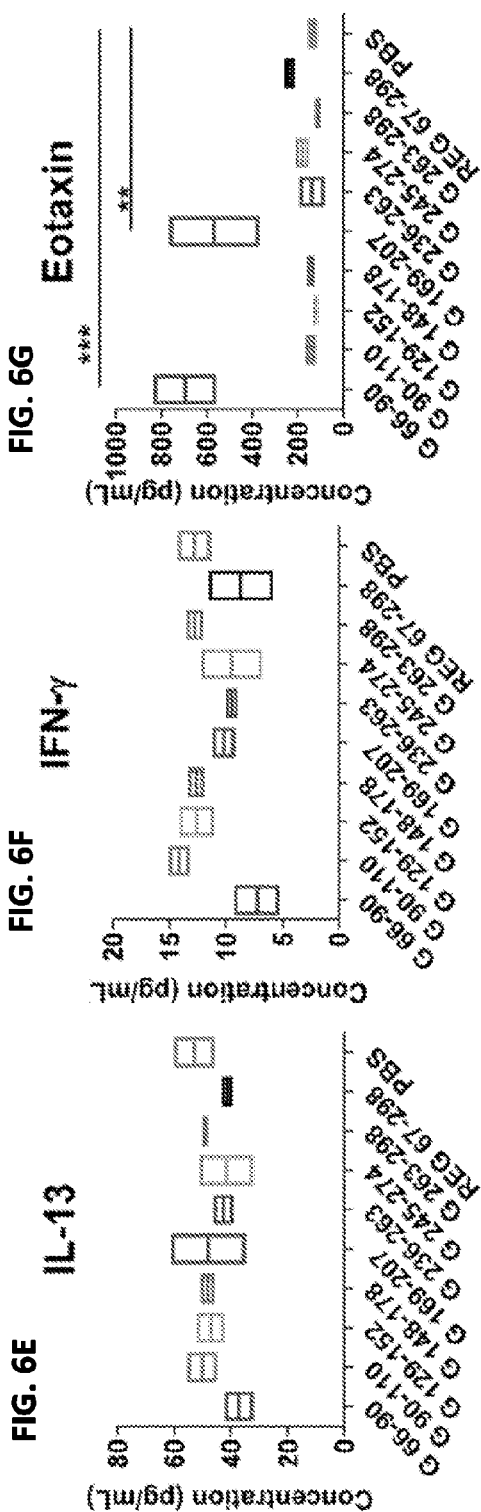
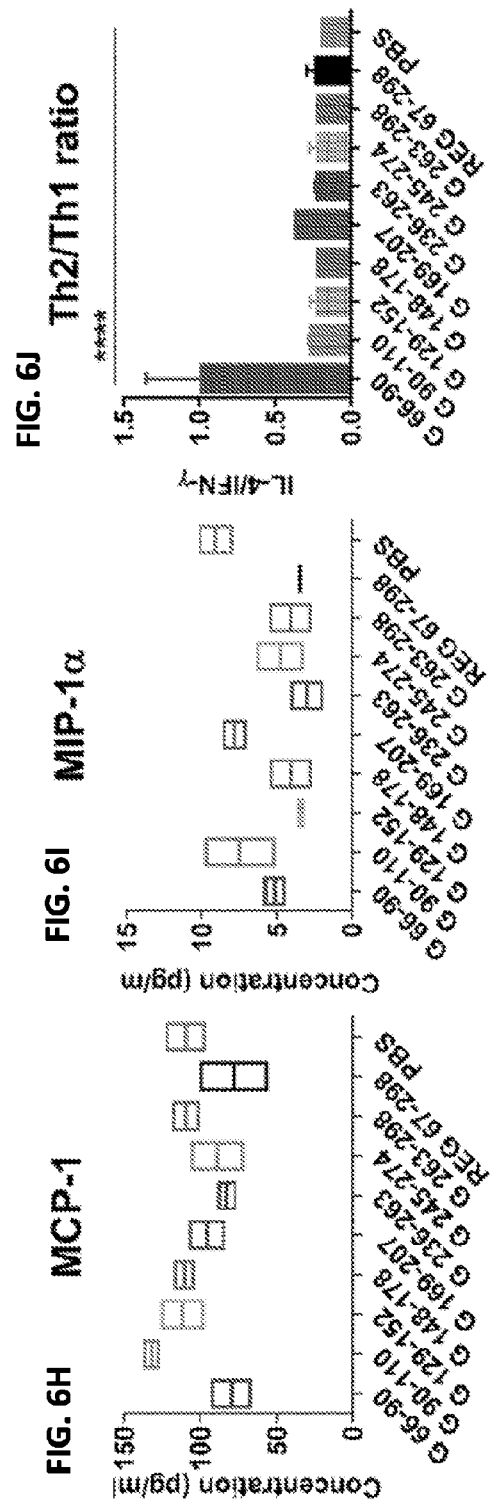

FIG. 7A

% inhibition of CX3CR1 binding to RMG

Rabbit sera

FIG. 7B

|  | Lungs-Flux (D5) | | Nasal Cavity-Flux (D5) | | Lung Viral Load Titer | |
|---|---|---|---|---|---|---|
|  | P Value | % compared to control (SD) | P Value | % compared to control (SD) | P Value | % compared to control (SD) |
| REG 67-298 | * | 32 (12.7) | ** | 33.6 (34.1) | **** | 1.1 (0.5) |
| REG ΔCCD | * | 38 (24.6) | *** | 21.9 (15.2) | **** | 1.2 (0.9) |
| REG 67-163 | * | 32 (12.9) | ** | 35.5 (20.7) | **** | 7.3 (11.5) |
| REG 187-298 | ns | 60 (28.8) | *** | 23.8 (11.4) | **** | 0.5 (0.8) |
| G 66-90 | ** | 32 (3.01) | ns | 60.8 (58.3) | **** | 0.1 (0) |
| G 90-110 | ** | 21.9 (1.56) | ns | 33.5 (7.2) | **** | 3.8 (1.8) |
| G 129-152 | ** | 24.7 (10.97) | ns | 34.3 (8.5) | **** | 0.13 (0.03) |
| G 148-178 | ** | 31.3 (14.83) | ns | 39.6 (14.83) | **** | 0.34 (0.2) |
| G169-207 | ns | 59.8 (40.47) | ns | 220 (228) | **** | 0.7 (1.1) |
| G 236-263 | ns | 51 (30.03) | ns | 38.8 (7.6) | **** | 1.43 (2.0) |
| G 245-274 | * | 39 (16.29) | ns | 37.1 (2.7) | **** | 0.22 (0.2) |
| G 263-298 | * | 42 (30.19) | ns | 62.0 (55.6) | **** | 0.71 (0.5) |

US 11,905,313 B2

SEQUENCE LISTING

<160> NUMBER OF SEQ ID NOS: 24

<210> SEQ ID NO 1
<211> LENGTH: 298
<212> TYPE: PRT
<213> ORGANISM: Respiratory Syncytial Virus

<400> SEQUENCE: 1

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295

<210> SEQ ID NO 2
<211> LENGTH: 227
<212> TYPE: PRT
<213> ORGANISM: Artificial Sequence
<220> FEATURE:
<223> OTHER INFORMATION: Recombinant RSV G protein

<400> SEQUENCE: 2

His Lys Val Thr Pro Thr Thr Ala Ile Ile Gln Asp Ala Thr Ser Gln
1               5                   10                  15

```
Ile Lys Asn Thr Thr Pro Thr Tyr Leu Thr Gln Asn Pro Gln Leu Gly
             20                  25                  30

Ile Ser Pro Ser Asn Pro Ser Glu Ile Thr Ser Gln Ile Thr Thr Ile
             35                  40                  45

Leu Ala Ser Thr Thr Pro Gly Val Lys Ser Thr Leu Gln Ser Thr Thr
 50                  55                  60

Val Lys Thr Lys Asn Thr Thr Thr Thr Gln Thr Gln Pro Ser Lys Pro
 65                  70                  75                  80

Thr Thr Lys Gln Arg Gln Asn Lys Pro Pro Ser Lys Pro Asn Asn Asp
                 85                  90                  95

Phe His Phe Glu Val Phe Asn Phe Val Gly Gly Gly Ser Gly Gly
                100                 105                 110

Gly Gly Ser Lys Arg Ile Pro Asn Lys Lys Pro Gly Lys Lys Thr Thr
            115                 120                 125

Thr Lys Pro Thr Lys Lys Pro Thr Leu Lys Thr Thr Lys Lys Asp Pro
130                 135                 140

Lys Pro Gln Thr Thr Lys Ser Lys Glu Val Pro Thr Thr Lys Pro Thr
145                 150                 155                 160

Glu Glu Pro Thr Ile Asn Thr Thr Lys Thr Asn Ile Ile Thr Thr Leu
                165                 170                 175

Leu Thr Ser Asn Thr Thr Gly Asn Pro Glu Leu Thr Ser Gln Met Glu
            180                 185                 190

Thr Phe His Ser Thr Ser Ser Glu Gly Asn Pro Ser Pro Ser Gln Val
            195                 200                 205

Ser Thr Thr Ser Glu Tyr Pro Ser Gln Pro Ser Ser Pro Pro Asn Thr
210                 215                 220

Pro Arg Gln
225

<210> SEQ ID NO 3
<211> LENGTH: 97
<212> TYPE: PRT
<213> ORGANISM: Artificial Sequence
<220> FEATURE:
<223> OTHER INFORMATION: Recombinant RSV G protein

<400> SEQUENCE: 3

His Lys Val Thr Pro Thr Thr Ala Ile Ile Gln Asp Ala Thr Ser Gln
 1               5                  10                  15

Ile

<223> OTHER INFORMATION: Recombinant RSV G protein

<400> SEQUENCE: 4

```
Lys Arg Ile Pro Asn Lys Lys P

```
                      165                 170                 175
Gly Gly Gly Gly Ser Lys Arg Ile Pro Asn Lys Lys Pro Gly Lys Lys
            180                 185                 190

Thr Thr Thr Lys Pro Thr Lys Lys Pro Thr Leu Lys Thr Thr Lys Lys
            195                 200                 205

Asp Pro Lys Pro Gln Thr Thr Lys Ser Lys Glu Val Pro Thr Thr Lys
    210                 215                 220

Pro Thr Glu Glu Pro Thr Ile Asn Thr Thr Lys Thr Asn Ile Ile Thr
225                 230                 235                 240

Thr Leu Leu Thr Ser Asn Thr Thr Gly Asn Pro Glu Leu Thr Ser Gln
                245                 250                 255

Met Glu Thr Phe His Ser Thr Ser Glu Gly Asn Pro Ser Pro Ser
            260                 265                 270

Gln Val Ser Thr Thr Ser Glu Tyr Pro Ser Gln Pro Ser Ser Pro Pro
            275                 280                 285

Asn Thr Pro Arg Gln
    290

<210> SEQ ID NO 7
<211> LENGTH: 29
<212> TYPE: PRT
<213> ORGANISM: Artificial Sequence
<220> FEATURE:
<223> OTHER INFORMATION: Transmembrane domain

<400> SEQUENCE: 7

Val Ala Gln Ile Thr Leu Ser Ile Leu Ala Met Ile Ile Ser Thr Ser
1               5                   10                  15

Leu Ile Ile Ala Ala Ile Ile Phe Ile Ala Ser Ala Asn
            20                  25

<210> SEQ ID NO 8
<211> LENGTH: 23
<212> TYPE: PRT
<213> ORGANISM: Artificial Sequence
<220> FEATURE:
<223> OTHER INFORMATION: Transmembrane domain

<400> SEQUENCE: 8

Ile Leu Ala Ile Tyr Ser Thr Val Ala Ser Ser Leu Val Leu Leu Val
1               5                   10                  15

Ser Leu Gly Ala Ile Ser Phe
            20

<210> SEQ ID NO 9
<211> LENGTH: 29
<212> TYPE: PRT
<213> ORGANISM: Artificial Sequence
<220> FEATURE:
<223> OTHER INFORMATION: Transmembrane domain

<400> SEQUENCE: 9

Ile Ile Thr Ile Gly Ser Ile Cys Met Val Val Gly Ile Ile Ser Leu
1               5                   10                  15

Ile Leu Gln Ile Gly Asn Ile Ile Ser Ile Trp Val Ser
            20                  25

<210> SEQ ID NO 10
<211> LENGTH: 66
<212> TYPE: PRT
<213> ORGANISM: Artificial Sequence
```

```
<220> FEATURE:
<223> OTHER INFORMATION: Transmembrane domain

<400> SEQUENCE: 10

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn
65

<210> SEQ ID NO 11
<211> LENGTH: 228
<212> TYPE: PRT
<213> ORGANISM: Artificial Sequence
<220> FEATURE:
<223> OTHER INFORMATION: Recombinant RSV G protein

<400> SEQUENCE: 11

His Lys Val Thr Leu Thr Thr Val Thr Val Gln Thr Ile Lys Asn His
1               5                   10                  15

Thr Glu Lys Asn Ile Thr Thr Tyr Leu Thr Gln Val Pro Pro Glu Arg
            20                  25                  30

Val Ser Ser Ser Lys Gln Pro Thr Thr Thr Ser Pro Ile His Thr Asn
        35                  40                  45

Ser Ala Thr Thr Ser Pro Asn Thr Lys Ser Glu Thr His His Thr Thr
    50                  55                  60

Ala Gln Thr Lys Gly Arg Thr Thr Thr Ser Thr Gln Thr Asn Lys Pro
65                  70                  75                  80

Ser Thr Lys Pro Arg Leu Lys Asn Pro Pro Lys Lys Pro Lys Asp Asp
                85                  90                  95

Tyr His Phe Glu Val Phe Asn Phe Val Gly Gly Gly Gly Ser Gly Gly
            100                 105                 110

Gly Gly Ser Lys Thr Ile Pro Ser Asn Lys Pro Lys Lys Lys Pro Thr
        115                 120                 125

Ile Lys Pro Thr Asn Lys Pro Thr Thr Lys Thr Thr Asn Lys Arg Asp
    130                 135                 140

Pro Lys Thr Pro Ala Lys Thr Thr Lys Lys Glu Thr Thr Thr Asn Pro
145                 150                 155                 160

Thr Lys Lys Pro Thr Leu Thr Thr Thr Glu Arg Asp Thr Ser Thr Ser
                165                 170                 175

Gln Ser Thr Val Leu Asp Thr Thr Thr Leu Glu His Thr Ile Gln Gln
            180                 185                 190

Gln Ser Leu His Ser Thr Thr Pro Glu Asn Thr Pro Asn Ser Thr Gln
        195                 200                 205

Thr Pro Thr Ala Ser Glu Pro Ser Thr Ser Asn Ser Thr Gln Asn Thr
    210                 215                 220

Gln Ser His Ala
225

<210> SEQ ID NO 12
<211> LENGTH: 97
<212> TYPE: PRT
```

```
<213> ORGANISM: Artificial Sequence
<220> FEATURE:
<223> OTHER INFORMATION: Recombinant RSV G protein

<400> SEQUENCE: 12

His Lys Val Thr Leu Thr Thr Val Thr Val Gln Thr Ile Lys Asn His
1               5                   10                  15

Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Pro Pro
                85                  90                  95

Glu Arg Val Ser Ser Ser Lys Gln Pro Thr Thr Thr Ser Pro Ile His
            100                 105                 110

Thr Asn Ser Ala Thr Thr Ser Pro Asn Thr Lys Ser Glu Thr His His
            115                 120                 125

Thr Thr Ala Gln Thr Lys Gly Arg Thr Thr Thr Ser Thr Gln Thr Asn
130                 135                 140

Lys Pro Ser Thr Lys Pro Arg Leu Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Thr Thr
            195                 200                 205

Lys Thr Thr Asn Lys Arg Asp Pro Lys Thr Pro Ala Lys Thr Thr Lys
210                 215                 220

Lys Glu Thr Thr Thr Asn Pro Thr Lys Lys Pro Thr Leu Thr Thr Thr
225                 230                 235                 240

Glu Arg Asp Thr Ser Thr Ser Gln Ser Thr Val Leu Asp Thr Thr Thr
                245                 250                 255

Leu Glu His Thr Ile Gln Gln Gln Ser Leu His Ser Thr Thr Pro Glu
            260                 265                 270

Asn Thr Pro Asn Ser Thr Gln Thr Pro Thr Ala Ser Glu Pro Ser Thr
            275                 280                 285

Ser Asn Ser Thr Gln Asn Thr Gln Ser His Ala
290                 295

<210> SEQ ID NO 15
<211> LENGTH: 294
<212> TYPE: PRT
<213> ORGANISM: Artificial Sequence
<220> FEATURE:
<223> OTHER INFORMATION: Recombinant RSV G protein

<400> SEQUENCE: 15

Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
50                  55                  60

Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Pro Pro
                85                  90                  95

Glu Arg Val Ser Ser Ser Lys Gln Pro Thr Thr Thr Ser Pro Ile His
            100                 105                 110

Thr Asn Ser Ala Thr Thr Ser Pro Asn Thr Lys Ser Glu Thr His His
            115                 120                 125

Thr Thr Ala Gln Thr Lys Gly Arg Thr Thr Thr Ser Thr Gln Thr Asn
    130                 135                 140

Lys Pro Ser Thr Lys Pro Arg Leu Lys Asn Pro Pro Lys Lys Pro Lys
145                 150                 155                 160

Asp Asp Tyr His Phe Glu Val Phe Asn Phe Val Gly Gly Gly Gly Ser
                165                 170                 175

Gly Gly Gly Gly Ser Lys Thr Ile Pro Ser Asn Lys Pro Lys Lys Lys
            180                 185                 190

Pro Thr Ile Lys Pro Thr Asn Lys Pro Thr Thr Lys Thr Thr Asn Lys
        195                 200                 205

Arg Asp Pro Lys Thr Pro Ala Lys Thr Thr Lys Lys Glu Thr Thr Thr
    210                 215                 220

Asn Pro Thr Lys Lys Pro Thr Leu Thr Thr Thr Glu Arg Asp Thr Ser
225                 230                 235                 240

Thr Ser Gln Ser Thr Val Leu Asp Thr Thr Thr Leu Glu His Thr Ile
                245                 250                 255

Gln Gln Gln Ser Leu His Ser Thr Thr Pro Glu Asn Thr Pro Asn Ser
            260                 265                 270

Thr Gln Thr Pro Thr Ala Ser Glu Pro Ser Thr Ser Asn Ser Thr Gln
        275                 280                 285

Asn Thr Gln Ser His Ala
    290

<210> SEQ ID NO 16
<211> LENGTH: 894
<212> TYPE: DNA
<213> ORGANISM: Respriatory Syncytial Virus

<400> SEQUENCE: 16
atgtcaaaaa ataaagacca acgcacggcg aaaaccctgg aacgcacctg ggataccctg      60
aatcatctgc tgttcatctc ctcctgcctg tataaactga atctgaaaag tgttgcacag     120
attaccctgt ccatcctggc tatgattatc agtacctccc tgattatcgc ggccatcatc     180
ttcatcgcaa gtgctaacca taaagtcacc ccgaccacgg cgattatcca ggatgccacc     240
tctcaaatca aaaacaccac gccgacgtac ctgacccaga tccgcaact gggcatttca     300 ccgtcgaacc cgtcagaaat cacctcgcag attaccacga tcctggcaag caccacgccg     360
ggtgtcaaaa gcacgctgca atctaccacg gtgaaaacca aaatccac gaccacgcag     420 acccaaccga gcaaaccgac cacgaaacag cgtcaaaata accgccgtc taaaccgaac     480 aatgattttc acttcgaagt gtttaacttc gttccgtgca gtatttgttc caacaatccg     540
acctgctggg ccatttgtaa acgcatcccg aacaaaaaac cgggcaagaa accacgacc     600 aaaccgacga aaaaccgac cctgaaaacg accaaaaaag acccgaaacc gcagacgacc     660
aaaagcaaag aagtgccgac gaccaaaccg acggaagaac cgaccattaa cacgaccaaa     720
accaatatta tcacgacccct gctgacctcc aacacgaccg gcaatccgga actgacctca     780
cagatggaaa cgttccattc gaccagctct gaaggtaatc gagcccgtc tcaggtcagc     840 acgacctccg aatacccgag ccagccgtct tctccgccga ataccccgcg tcag          894

<210> SEQ ID NO 17
<211> LENGTH: 879
<212> TYPE: DNA
<213> ORGANISM: Artificial Sequence
<220> FEATURE:
<223> OTHER INFORMATION: Recombinant RSV G protein encoding sequence

<400> SEQUENCE: 17

```
atgtcaaaaa ataaagacca acgcacggcg aaaaccctgg aacgcacctg ggataccctg 60
aatcatctgc tgttcatctc ctcctgcctg tataaactga atctgaaaag tgttgcacag 120
attaccctgt ccatcctggc tatgattatc agtacctccc tgattatcgc ggccatcatc 180
ttcatcgcaa gtgctaacca taaagtcacc ccgaccacgg cgattatcca ggatgccacc 240
tctcaaatca aaaacaccac gccgacgtac ctgacccaga atccgcaact gggcatttca 300
ccgtcgaacc cgtcagaaat cacctcgcag attaccacga tcctggcaag caccacgccg 360
ggtgtcaaaa gcacgctgca atctaccacg gtgaaaacca aaaataccac gaccacgcag 420
acccaaccga gcaaaccgac cacgaaacag cgtcaaaata aaccgccgtc taaaccgaac 480
aatgattttc acttcgaagt gtttaacttc gttggtggtg gcggctccgg tggcggtggt 540
agcaaacgca tcccgaacaa aaaaccgggc aagaaaacca cgaccaaacc gacgaaaaaa 600
ccgaccctga aaacgaccaa aaaagacccg aaaccgcaga cgaccaaaag caaagaagtg 660
ccgacgacca aaccgacgga agaaccgacc attaacacga ccaaaaccaa tattatcacg 720
accctgctga cctccaacac gaccggcaat ccggaactga cctcacagat ggaaacgttc 780
cattcgacca gctctgaagg taatccgagc ccgtctcagg tcagcacgac ctccgaatac 840
ccgagccagc cgtcttctcc gccgaatacc ccgcgtcag 879
```

<210> SEQ ID NO 18
<211> LENGTH: 693
<212> TYPE: DNA
<213> ORGANISM: Artificial Sequence
<220> FEATURE:
<223> OTHER INFORMATION: Recombinant RSV G protein encoding sequence

<400> SEQUENCE: 18

```
atggcggccg cacataaagt caccccgacc acggcgatta tccaggatgc cacctctcaa 60
atcaaaaaca ccacgccgac gtacctgacc cagaatccgc aactgggcat ttcaccgtcg 120
aacccgtcag aaatcacctc gcagattacc acgatcctgg caagcaccac gccgggtgtc 180
aaaagcacgc tgcaatctac cacggtgaaa accaaaaata ccacgaccac gcagacccaa 240
ccgagcaaac cgaccacgaa acagcgtcaa aataaaccgc cgtctaaacc gaacaatgat 300
tttcacttcg aagtgtttaa cttcgttggt ggtggcggct ccggtggcgg tggtagcaaa 360
cgcatcccga acaaaaaacc gggcaagaaa accacgacca aaccgacgaa aaaaccgacc 420
ctgaaaacga ccaaaaaaga cccgaaaccg cagacgacca aaagcaaaga agtgccgacg 480
accaaaccga cggaagaacc gaccattaac acgaccaaaa ccaatattat cacgaccctg 540
ctgacctcca acacgaccgg caatccggaa ctgacctcac agatggaaac gttccattcg 600
accagctctg aaggtaatcc gagcccgtct caggtcagca cgacctccga atacccgagc 660
cagccgtctt ctccgccgaa taccccgcgt cag 693

<210> SEQ ID NO 19
<211> LENGTH: 291
<212> TYPE: DNA
<213> ORGANISM: Artificial Sequence
<220> FEATURE:
<223> OTHER INFORMATION: Recombinant RSV G protein encoding sequence
<400> SEQUENCE: 19
cataaagtca ccccgaccac ggcgattatc caggatgcca cctctcaaat caaaaacacc 60
acgccgacgt acctgaccca gaatccgcaa ctgggcattt caccgtcgaa cccgtcagaa 120

| atcacctcgc agattaccac gatcctggca agcaccacgc cgggtgtcaa aagcacgctg | 180 |
| caatctacca cggtgaaaac caaaaatacc acgaccacg agacccaacc gagcaaaccg | 240 |
| accacgaaac agcgtcaaaa taaaccgccg tctaaaccga acaatgattt t | 291 |

<210> SEQ ID NO 20
<211> LENGTH: 336
<212> TYPE: DNA
<213> ORGANISM: Artificial Sequence
<220> FEATURE:
<223> OTHER INFORMATION: Recombinant RSV G protein encoding sequence

<400> SEQUENCE: 20

| aaacgcatcc cgaacaaaaa accgggcaag aaaaccacga ccaaaccgac gaaaaaaccg | 60 |
| accctgaaaa cgaccaaaaa agacccgaaa ccgcagacga ccaaaagcaa agaagtgccg | 120 |
| acgaccaaac cgacggaaga accgaccatt aacacgacca aaaccaatat tatcacgacc | 180 |
| ctgctgacct ccaacacgac cggcaatccg gaactgacct cacagatgga aacgttccat | 240 |
| tcgaccagct ctgaaggtaa tccgagcccg tctcaggtca gcacgacctc cgaatacccg | 300 |
| agccagccgt cttctccgcc gaatacccg cgtcag | 336 |

<210> SEQ ID NO 21
<211> LENGTH: 897
<212> TYPE: DNA
<213> ORGANISM: Respiratory Syncytial Virus

<400> SEQUENCE: 21

| atgtcaaaac acaaaaacca acgcaccgcc cgcacgctgg aaaaaacctg ggatacgctg | 60 |
| aaccatctga ttgtcatctc gtcctgcctg tatcgtctga acctgaaaag cattgcacaa | 120 |
| atcgctctgt ctgtgctggc aatgattatc tccacctcac tgattatcgc ggccatcatc | 180 |
| ttcatcatca gtgctaacca taaagttacc ctgaccacgg tgacggttca gaccattaaa | 240 |
| aaccacaccg agaaaaacat caccacgtac ctgacccaag ttccgccgga acgcgtcagc | 300 |
| tctagtaaac agccgaccac gaccagcccg attcatacca actcagcgac gacctcgccg | 360 |
| aatacgaaat ctgaaaccca tcacgacc gcccaaacca aaggccgtac gaccacgagt | 420 |
| acgcagacca acaaaccgtc caccaaaccg cgcctgaaaa atccgccgaa aaaaccgaaa | 480 |
| gatgactatc acttcgaagt ctttaacttc gtgccgtgca gcatttgtgg taacaatcag | 540 |
| ctgtgcaaat caatttgtaa aaccatcccg tcgaataaac cgaagaaaaa accgacgatc | 600 |
| aaaccgacca caaaccgac cacgaaaacc acgaataaac gtgatccgaa acccccggca | 660 |
| aaaccaccag agaaagaaac cacgaccaac ccgacgaaaa accgaccct gacgaccacg | 720 |
| gaacgcgata cgtcgaccag ccaatctacc gtcctggaca ccacgacct ggaacatacc | 780 |
| attcagcaac agagtctgca ctccacgacc ccggaaaaca cgccgaatag cacccagacc | 840 |
| ccgaccgcaa gcgaaccgag caccagcaac tccacccaaa acacccaatc ccacgca | 897 |

<210> SEQ ID NO 22
<211> LENGTH: 699
<212> TYPE: DNA
<213> ORGANISM: Artificial Sequence
<220> FEATURE:
<223> OTHER INFORMATION: Recombinant RSV G protein encoding sequence

<400> SEQUENCE: 22

| cataaagtta ccctgaccac ggtgacggtt cagaccatta aaaaccacac cgagaaaaac | 60 |

```
atcaccacgt acctgaccca agttccgccg aacgcgtca gctctagtaa acagccgacc    120
acgaccagcc cgattcatac caactcagcg acgacctcgc cgaatacgaa atctgaaacc    180
catcacacga ccgcccaaac caaaggccgt acgaccacga gtacgcagac caacaaaccg    240
tccaccaaac cgcgcctgaa aaatccgccg aaaaaaccga agatgactac tcacttcgaa    300
gtctttaact tcgtgccgtg cagcatttgt ggtaacaatc agctgtgcaa atcaatttgt    360
aaaaccatcc cgtcgaataa accgaagaaa aaaccgacga tcaaaccgac caacaaaccg    420
accacgaaaa ccacgaataa acgtgatccg aaaaccccgg caaaaaccac caagaaagaa    480
accacgacca cccgacgaa aaaaccgacc ctgacgacca cggaacgcga tacgtcgacc    540
agccaatcta ccgtcctgga caccacgacc ctggaacata ccattcagca acagagtctg    600
cactccacga ccccggaaaa cacgccgaat agcacccaga ccccgaccgc aagcgaaccg    660
agcaccagca actccaccca aaacacccaa tcccacgca                           699
```

<210> SEQ ID NO 23
<211> LENGTH: 882
<212> TYPE: DNA
<213> ORGANISM: Artificial Sequence
<220> FEATURE:
<223> OTHER INFORMATION: Recombinant RSV G protein encoding sequence

<400> SEQUENCE: 23

```
atgtcaaaac acaaaaacca acgcaccgcc cgcacgctgg aaaaaacctg ggatacgctg    60
aaccatctga ttgtcatctc gtcctgcctg tatcgtctga acctgaaaag cattgcacaa    120
atcgctctgt ctgtgctggc aatgattatc tccacctcac tgattatcgc ggccatcatc    180
ttcatcatca gtgctaacca taaagttacc ctgaccacgg tgacggttca gaccattaaa    240
aaccacaccg agaaaaacat caccacgtac ctgacccaag ttccgccgga acgcgtcagc    300
tctagtaaac agccgaccac gaccagcccg attcatacca actcagcgac gacctcgccg    360
aatacgaaat ctgaaaccca tcacacgacc gcccaaacca aaggccgtac gaccacgagt    420
acgcagacca caaaccgtc caccaaaccg cgcctgaaaa atccgccgaa aaaaccgaaa    480
gatgactatc acttcgaagt ctttaacttc gtgggtggtg cggctccgg tggcggtggt    540 agcaaaacca tcccgtcgaa taaaccgaag aaaaaaccga cgatcaaacc gaccaacaaa    600
ccgaccacga aaaccacgaa taaacgtgat ccgaaaaccc cggcaaaaac caccaagaaa    660
gaaaccacga cccacccgac gaaaaaaccg accctgacga ccacggaacg cgatacgtcg    720
accagccaat ctaccgtcct ggacaccacg accctggaac ataccattca gcaacagagt    780
ctgcactcca cgaccccgga aaacacgccg aatagcaccc agaccccgac cgcaagcgaa    840
ccgagcacca gcaactccac ccaaaacacc caatcccacg ca                       882
```

<210> SEQ ID NO 24
<211> LENGTH: 684
<212> TYPE: DNA
<213> ORGANISM: Artificial Sequence
<220> FEATURE:
<223> OTHER INFORMATION: Recombinant RSV G protein encoding sequence

<400> SEQUENCE: 24

```
cataaagtta ccctgaccac ggtgacggtt cagaccatta aaaaccacac cgagaaaaac    60
atcaccacgt acctgaccca agttccgccg aacgcgtca gctctagtaa acagccgacc    120
acgaccagcc cgattcatac caactcagcg acgacctcgc cgaatacgaa atctgaaacc    180
catcacacga ccgcccaaac caaaggccgt acgaccacga gtacgcagac caacaaaccg    240
```

-continued

```
tccaccaaac cgcgcctgaa aaatccgccg aaaaaaccga aagatgacta tcacttcgaa      300
gtctttaact tcgtgggtgg tggcggctcc ggtggcggtg gtagcaaaac catcccgtcg      360
aataaaccga agaaaaaacc gacgatcaaa ccgaccaaca aaccgaccac gaaaaccacg      420
aataaacgtg atccgaaaac cccggcaaaa accaccaaga aagaaccac gaccaacccg       480 acgaaaaaac cgaccctgac gaccacggaa cgcgatacgt cgaccagcca atctaccgtc      540
ctggacacca cgaccctgga acataccatt cagcaacaga gtctgcactc cacgacccg      600 gaaaacacgc cgaatagcac ccagacccg accgcaagcg aaccgagcac cagcaactcc      660
acccaaaaca cccaatccca cgca                                            684
```

RECOMBINANT RSV G PROTEINS AND THEIR USE

CROSS REFERENCE TO RELATED APPLICATION

This is the U.S. National Stage of International Application No. PCT/US2018/062623, filed Nov. 27, 2018, which was published in English under PCT Article 21(2), which in turn claims the benefit of U.S. Provisional Application No. 62/591,533, filed Nov. 28, 2017. The provisional application is incorporated by reference herein in its entirety.

FIELD

This disclosure relates to polypeptides, polynucleotides, compositions, and methods of their use for elicitation and detection of an immune response to respiratory syncytial virus (RSV).

BACKGROUND

Respiratory syncytial virus (RSV) is an enveloped non-segmented negative-strand RNA virus in the family Paramyxoviridae, genus *Pneumovirus*. It is the most common cause of bronchiolitis and pneumonia among children in their first year of life. RSV also causes repeated infections including severe lower respiratory tract disease, which may occur at any age, especially among the elderly or those with compromised cardiac, pulmonary, or immune systems. Passive immunization currently is used to prevent severe illness caused by RSV infection, especially in infants with prematurity, bronchopulmonary dysplasia, or congenital heart disease. Despite repeated efforts, an effective vaccine to RSV is not available.

SUMMARY

Disclosed herein are recombinant RSV G ectodomains and fragment thereof that are shown to elicit a neutralizing/protective immune response to RSV in mammalian subjects. The recombinant RSV G ectodomains and fragments thereof have superior properties for production, such as the absence of glycosylation and a transmembrane domain, yet remain immunogenic and promote a $Th_1$-biased immune response. In several embodiments, the immune response inhibits disease in the lower respiratory tract. Thus, the disclosed recombinant RSV G ectodomains provide an unexpectedly superior combination of immunogenicity, solubility, and production capacity.

In some embodiments, the recombinant RSV G ectodomain comprises a deletion of residues 172-186 with residues 171 and 187 linked by a peptide linker; for example, the recombinant RSV G ectodomain comprises, consists essentially of, or consists of RSV G residues 67-171 linked to RSV G residues 187-298 by the peptide linker. The recombinant RSV G ectodomain can be, for example, a bovine RSV G ectodomain, a human subtype A RSV G ectodomain, or a human subtype B RSV G ectodomain, containing the deletion of residues 172-186 with residues 171 and 187 linked by the peptide linker A non-limiting example of a peptide linker that can be used in the disclosed embodiments is set forth as SEQ ID NO: 5 (GGGGSGGGGS). In some embodiments, the recombinant RSV G ectodomain comprises, consists essentially of, or consists of the amino acid sequence set forth as SEQ ID NO: 2 or SEQ ID NO: 11. In some embodiments, the recombinant RSV G ectodomain comprises, consists essentially of, or consists of an amino acid sequence at least 90% (such as at least 95%) identical to SEQ ID NO: 2 or SEQ ID NO: 11.

In several embodiments, the recombinant RSV G ectodomain or fragment thereof is not glycosylated. For example, the recombinant RSV G ectodomain or fragment thereof is produced in a bacterial expression system that does not lead to glycosylation of the expressed protein.

In some embodiments, the RSV G ectodomain is soluble in aqueous solution, for example, the recombinant RSV G ectodomain does not include a transmembrane domain or cytosolic tail. In additional embodiments, the recombinant RSV G ectodomain or fragment thereof is membrane anchored, for example by linkage to an N-terminal transmembrane domain and cytosolic tail, such as a RSV G transmembrane domain and cytosolic tail.

Immunogenic compositions including the recombinant RSV G ectodomain or fragment thereof that are suitable for administration to a subject are also provided, and may also be contained in a unit dosage form. The compositions can further include an adjuvant. The immunogenic compositions can also include additional immunogens, such as a RSV F protein. The recombinant RSV G ectodomains may also be conjugated to a carrier to facilitate presentation to the immune system.

Methods of inducing an immune response to RSV by administering to a subject an effective amount of a disclosed recombinant RSV G ectodomain or fragment thereof, or related nucleic acid molecule or vector are also provided.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1F. Recombinant G proteins produced in *E. coli*. (FIGS. 1A-1B) Schematic representation of the RSV G protein and subdomains. RSV G ectodomain lacks the cytoplasmic and transmembrane domains (CT-TM) and is not glycosylated (REG) since it is produced in *E. coli*. REG 67-298, REG 67-298 with aa 172-186 deleted (REG ΔCCD), REG N-terminus (aa 67-163), and REG C-terminus (aa 187-298), all containing 6× His tag at C-terminus, were expressed in *E. coli* and purified using a Ni-NTA column, and subjected to SDS-PAGE under reducing conditions. (FIGS. 1C-1D) Superdex 200 10/300 gel filtration chromatography of RSV G proteins produced in the bacterial system (REGs). Elution profiles of purified REG 67-298 and REG ΔCCD (FIG. 1C), REG 67-163 and REG 187-298 (FIG. 1D) are overlaid with molecular weight standards (gray dotted line). (FIG. 1E) Neutralizing antibody response following REG 67-298, REG ΔCCD, REG 67-163, and REG 187-298 immunizations in rabbits by PRNT assay. Serum samples were collected from individual rabbits 8 days after the first (IM1), second (IM2), and third (IM3) immunizations, and were tested for neutralization by PRNT against the RSV A2 strain. Neutralizing antibody titers represent 50% plaque inhibition. (FIG. 1F) SPR analysis of post-third vaccination serum antibodies (diluted 10-fold) binding to fully glycosylated G ectodomain RMG from RSV-A2.

FIGS. 2A-2J. Recombinant G protein immunization and challenge study in mice. (FIG. 2A) Schematic representation of mouse immunization and challenge schedule. BALB/c mice (N=8 per group) were immunized i.m. with 20 μg of REG 67-298, REG ΔCCD, REG 67-163, and REG 187-298 from RSV strain A2 with Emulsigen adjuvant, or with PBS as a control. After the second immunization, blood was collected from the tail veins. Then, mice were challenged intranasally with $10^6$ PFU of RSV rA2-Line-19F-FFL expressing the homologous G protein. In vivo imaging of lungs and the nasal cavity was performed daily for 5 days following RSV infection. Mice were sacrificed on day 5 post-challenge, when lungs and blood were collected. (FIGS. 2B and 2D) Live whole body imaging was performed to detect firefly luciferase activity in the lungs (FIG. 2B) and nasal cavity (FIG. 2D). Graphs represent the quantification of total flux (photons/sec) on day 5 post challenge. 50% and 30% of the mean flux value of the PBS control group is indicated by the two dotted lines. The lowest grey lines (UC) represents the average flux values of the uninfected control mice ($5.23 \times 10^4$ for lungs and $1.11 \times 10^4$ for nasal cavity). (FIG. 2C) Lung viral loads at 5 days post-viral challenge as measured by plaque assay. (FIG. 2E) Serum samples were collected from individual mice after the second immunization and were tested for neutralization by PRNT against RSV A2 strain in A549 cells. Neutralizing antibody titers represent 50% inhibition of plaque numbers. The average for each group is indicated by a horizontal line. The dotted lines indicate cutoff values based on the 1:20 dilution of sera used in PRNT. (FIGS. 2F-2G) The same serum samples were analyzed by ELISA using plates coated with purified RSV rA2-Line19F-FFL (FIG. 2F) or RSV-B1 (FIG. 2G) virion particles. The serum samples were serially diluted and the detection of antibodies were measured by absorbance at 490 nm. The mean absorbance +SD for each dilution is indicated. (FIG. 2H) End-point titers of the serum samples were determined as the reciprocal of the highest dilution providing an optical density (OD) twice that of the negative control. (FIGS. 2I-2J) Correlation between endpoint titer (Log2) and viral load measured by plaque assay in lungs on day 5 post-challenge (FIG. 2I) or bioluminescence flux signal in the nasal cavity on day 5 post-challenge (FIG. 2J). REG 67-298 group is indicated by black triangles, REG ΔCCD by blue triangles, REG 67-163 by yellow circles, REG 187-298 by green squares, and PBS by red rhombuses. Inverse Spearman correlations were observed between endpoint titers measured by ELISA vs. Lung viral loads ($r=-0.5622$; $p=0.0152$) (FIG. 2I) and vs. Nasal Cavity Fluxes ($r=-0.4043$; $p=0.0860$) (FIG. 2J). Statistical significance was tested by one-way ANOVA and Bonferroni multiple-comparison tests. **, $p<0.0001$; *; $p<0.001$; **, $p<0.01$; *, $p<0.05$.

FIGS. 3A-3J. Histopathology and cytokine/chemokine levels in the lungs of animals vaccinated with the REG 67-298, REG ΔCCD, REG 67-163, and REG 187-298 at day 5 following RSV challenge. (FIG. 3A) Lung tissues were collected at 5 days post-challenge and were stained with hematoxylin and eosin. Individual lungs were scored for pulmonary inflammation: bronchiolitis (mucous metaplasia of bronchioles), perivasculitis (inflammatory cell infiltration around the small blood vessels), interstitial pneumonia (inflammatory cell infiltration and thickening of alveolar walls), and alveolitis (cells within the alveolar spaces). Slides were scored blindly using a 0-4 severity scale. The scores were subsequently converted to a 0-100% histopathology scales. (FIGS. 3B-3I) Levels of cytokines and chemokines in lung homogenates from day 5 post challenge were measured in a Bio-Plex Pro mouse cytokine assay. Values are cytokine/chemokine concentrations, expressed in pictograms per milliliter. The mean for each group is shown. (FIG. 3J) Ratio of the observed concentrations of IL-4 vs. IFNγ shown in FIGS. 3B and 3F. Statistical significance was tested by one-way ANOVA and Bonferroni multiple-comparison tests. *, $p<0.05$.

(FIG. 4A) Schematic diagram of RSV G peptides, conjugated to KLH, that were used to immunize rabbits, combined with Emulsigen adjuvant. (FIG. 4B) SPR analysis of post-third vaccination serum antibodies (diluted 10-fold) to RMG from RSV A2 strain. (FIG. 4C) Virus neutralization titers following first, (IM1), second (IM2) and third (IM3) vaccinations. Titer is shown for 50% reduction in number of plaques.

FIGS. 5A-5I. RSV G peptide immunization and challenge study in mice. (FIG. 5A) Schematic representation of mouse immunization and challenge schedule. BALB/c mice (N=6 per group) were immunized i.m. with 25 µg of KLH-conjugated peptides: G 66-90, G 90-110, G 129-152, G 148-178, G 169-207, G 236-263, G 245-274, G 263-298 or with 20 µg of RSV strain A2 REG 67-298 with Emulsigen adjuvant, or with PBS as a control. After the second immunization, blood was collected from the tail veins. Then, mice were challenged intranasally with $10^6$ PFU of RSV rA2-Line19F-FFL. In vivo imaging of lungs was performed daily for 5 days following RSV infection. Mice were sacrificed on day 5 post-challenge, when lungs and blood were collected. (FIG. 5B) Serum samples were collected from individual mice after second immunization and antibodies were analyzed using ELISA plates coated with purified RSV rA2-Line-19F-FFL. The serum samples were serially diluted and the detection of antibodies were measured by absorbance at 490 nm. The mean +SD absorbance for each dilution is indicated. (FIG. 5C) End-point titers of the serum samples were determined as the reciprocal of the highest dilution providing an OD twice that of the negative control. (FIGS. 5D and 5F) Live whole body imaging was performed daily to detect firefly luciferase activity in the lungs (FIG. 5D) and nasal cavity (FIG. 5F) on day 5 post challenge. Graphs represent the quantification of total flux (photons). 50% and 30% of the mean flux value of the PBS control group is indicated by the two dotted lines. The lowest grey line labeled 'UC' represents the average flux values of the uninfected control mice ($3.74 \times 10^4$ for lungs and $1.48 \times 10^4$ for nasal cavity). (FIG. 5E) Lung viral loads at 5 days post-viral challenge as measured by plaque assay. Statistical significance was tested by one-way ANOVA and Bonferroni multiple-comparison tests. **, $p<0.0001$; *, $p<0.001$; **, $p<0.01$ *, $p<0.05$. (FIGS. 5G-5I) Correlation between ELISA endpoint titer (Log2) and bioluminescence flux signal in lungs (FIG. 5G) or nasal cavity (FIG. 5I) on day 5 post-challenge, or viral load measured by plaque assay in lungs on day 5 post-challenge (FIG. 5H). The symbol colors correspond to the groups shown in (FIGS. 5D-5F). Inverse Spearman correlations were observed between endpoint titers measured by ELISA vs. Lung Fluxes ($r=-0.2935$; $p=0.1223$) (FIG. 5G) and vs. Lung viral loads ($r=-0.4835$; $p=0.0053$) (H) and vs. Nasal Cavity Fluxes ($r=-0.0532$; $p=0.0.7880$) (FIG. 5I).

FIGS. 6A-6J. Histopathology and cytokine/chemokine levels in the lungs of animals vaccinated with the RSV G peptides at day 5 following RSV challenge. (FIG. 6A) Lung tissues were collected at 5 days post-challenge and were stained with hematoxylin and eosin. Individual lungs were scored for pulmonary inflammation: bronchiolitis (mucous metaplasia of bronchioles), perivasculitis (inflammatory cell infiltration around the small blood vessels), interstitial pneumonia (inflammatory cell infiltration and thickening of alveolar walls), and alveolitis (cells within the alveolar spaces). Slides were scored blindly using a 0-4 severity scale. The scores were subsequently converted to a 0-100% histopathology scales. (FIGS. 6B-6I) Levels of cytokines and chemokines in lung homogenates from day 5 post challenge were measured in a Bio-Plex Pro mouse cytokine assay. Values are cytokine/chemokine concentrations, expressed in picograms per milliliter The mean for each group is shown. (FIG. 6J) Ratio of the observed concentrations of IL-4 vs. IFNγ shown in panels 6B and 6F. Statistical significance was tested by one-way ANOVA and Bonferroni multiple comparison tests. **, p<0.0001; *, p<0.001; **, p<0.01; *, p<0.05.

FIGS. 7A and 7B. Serum antibodies generated against different G immunogens can block interaction between glycosylated RSV-G (RMG) and recombinant CX3CR1 receptor. (FIG. 7A) SPR assay was performed with the recombinant RSV-G protein from 293T cells (RMG) captured on a HTG sensor chip followed by addition of post-2nd immunization rabbit sera (10-fold dilution). The binding of recombinant CX3CR1 to the antibody bound RMG was then measured by SPR. Pre-vaccination animal sera were used as a negative control. Total CX3CR1 binding to RMG in absence of any antibody binding was defined as 100%. Percentage inhibition for the pre-and post-vaccination rabbit sera was determined. (FIG. 7B) The mean flux values in lungs, nasal cavity, and the mean lung viral loads on day 5 post challenge of each group were compared to the PBS group set as 100%. Statistical significance when compared to the PBS group was tested by one-way ANOVA and Bonferroni multiple-comparison tests, **, p<0.0001; *, p<0.001; **, p<0.01*, p<0.05; ns, not significant.

SEQUENCE LISTING

Figure 1A:
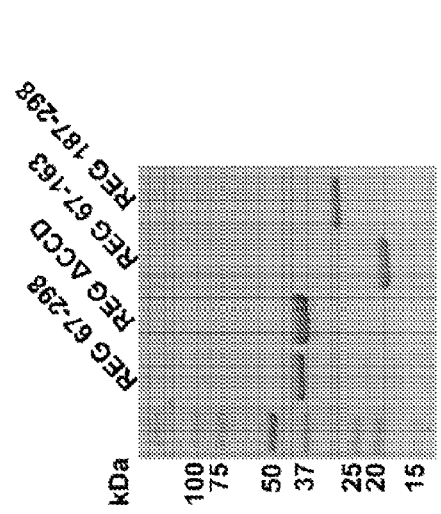

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~32 kb), which was created on Apr. 22, 2020, and which is incorporated by reference herein.

DETAILED DESCRIPTION

Disclosed herein are embodiments of RSV G-based immunogens that provide superior properties for production, such as the absence of glycosylation and a transmembrane domain, yet remain immunogenic in mammals and promote a $Th_1$-biased immune response. Thus, the disclosed recombinant RSV G proteins provide an unexpectedly superior combination of immunogenicity, solubility, and production capacity. In some embodiments, the recombinant RSV G ectodomain trimers provided herein can be used to induce an immune response in a subject that protects from subsequent RSV infection and/or reduces the symptoms of a subsequent RSV infection, particularly in the lower respiratory tract. In additional embodiments, the recombinant RSV G ectodomain trimers provided herein can be used as probes to identify the presence of RSV G specific antibodies in a sample, for example, to confirm successful; immunization of a subject with an RSV G vaccine.

RSV-G protein without the CX3CR1 binding central conserved domain (CCD) (aa 172-186) were immunogenic in rabbits, and in mice these proteins significantly protected animals from RSV challenge as measured by reduced viral loads in the lungs and nasal cavity; wherein protection also correlated with virion binding antibodies. Furthermore, a very low Th2/Th1 cytokine ratio was measured in the lungs of vaccinated animals on day 5 post RSV challenge suggesting contribution to protection from pathology that was similar to REG protein containing the CCD motif (REG 67-298). Thus, the CCD motif can be deleted without a significant impact on protective efficacy following immunization with REG vaccine.

Moreover, the two immunodominant non-glycosylated subdomains (aa 67-163 and aa187-298) flanking the CCD motif were immunogenic and generated antibodies that bound to fully glycosylated RMG when tested using SPR and to virions in ELISA. Although corresponding neutralization titers were weak based on in vitro assays, in the mouse challenge studies the N-terminal subdomain (67-163) showed better protection than the C-terminal domain (187-298) when lung flux values were compared to the mock-immunized control. Further, synthetic, unglycosylated G peptides containing mostly non-conformational antigenic sites upstream and downstream of the CCD were immunogenic in rabbits and generated antibodies that bound the fully glycosylated recombinant G protein produced in mammalian cells (RMG) as well as intact RSV A2 line 19F virions in ELISA. Mice immunized with G peptides located in N-terminal of CCD showed better protection (lung viral load fluxes≤30% of those seen in the PBS mock control), than antigenic site peptides located in the C-terminal of CCD (with viral loads that were 40-50% of control). Taken together, these data suggest that antigenic sites in the N-terminal domain of G protein may contribute to protection against RSV.

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references. As used herein, the singular forms "a," "an," and "the," refer to both the singular as well as plural, unless the context indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Adjuvant: A vehicle used to enhance antigenicity. Adjuvants include, for example, a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. It also includes Oil in water or other adjuvants including but not limited to MF59, matrix, AS, Emulsigne, Addavax etc. The person of ordinary skill in the art is familiar with adjuvants (see, e.g., Singh (ed.) Vaccine Adjuvants and Delivery Systems. Wiley-Interscience, 2007). Adjuvants can be used in combination with the disclosed recombinant.

Administration: The introduction of a composition into a subject by a chosen route. Administration can be local or systemic. For example, if the chosen route is intranasal, the composition (such as a composition including a disclosed recombinant RSV G ectodomain) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution and deletion: An amino acid substitution is the replacement of an amino acid in a polypeptide with one or more different amino acids. In some examples, an amino acid in a polypeptide is substituted with an amino acid from a homologous polypeptide, for example, an amino acid in a recombinant group A RSV G polypeptide can be substituted with the corresponding amino acid from a group B RSV G polypeptide. An amino acid deletion is the removal of one or more amino acids from a polypeptide, typically using molecular biology techniques.

Antibody: An immunoglobulin, antigen-binding fragment, or derivative thereof, that specifically binds and recognizes an analyte (antigen) such as RSV G protein, an antigenic fragment thereof, or a dimer or multimer of the antigen. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

Carrier: An immunogenic molecule to which an immunogen can be linked. When linked to a carrier, the antigen may become more immunogenic. Carriers are chosen to increase the immunogenicity of the antigen and/or to elicit antibodies against the carrier which are diagnostically, analytically, and/or therapeutically beneficial. Useful carriers include polymeric carriers, which can be natural (for example, proteins from bacteria or viruses), semi-synthetic or synthetic materials containing one or more functional groups to which a reactant moiety can be attached.

Conservative amino acid substitution: "Conservative" amino acid substitutions are those substitutions that do not substantially affect or decrease a function of a protein, such as the ability of the protein to induce an immune response when administered to a subject. The term conservative also includes the use of a substituted amino acid in place of an unsubstituted parent amino acid. Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

The following six groups are examples of amino acids that are considered to be conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).

Non-conservative substitutions are those that reduce an activity or function of the recombinant RSV G ectodomain, such as the ability to induce an immune response when administered to a subject. For instance, if an amino acid residue is essential for a function of the protein, even an otherwise conservative substitution may disrupt that activity. Thus, a conservative substitution does not alter the basic function of a protein of interest.

Consists essentially of and Consists Of: A polypeptide comprising an amino acid sequence that consists essentially of a specified amino acid sequence does not include any additional amino acid residues. However, the residues in the polypeptide can be modified to include non-peptide components, such as labels (for example, fluorescent, radioactive, or solid particle labels), sugars or lipids, and the N-or C-terminus of the polypeptide can be joined (for example, by peptide bond) to a heterologous amino acid, such as a cysteine (or other) residue in the context of a linker for conjugation chemistry. A polypeptide that consists of a specified amino acid sequence does not include any additional amino acid residues, nor does it include additional biological components, such as nucleic acids lipids, sugars, nor does it include labels. However, the N-or C-terminus of the polypeptide can be joined (for example, by peptide bond) to a heterologous amino acid, such as a peptide tag, or a cysteine (or other) residue in the context of a linker for conjugation chemistry. A polypeptide that consists or consists essentially of a specified amino acid sequence can be glycosylated or have an amide modification.

Control: A reference standard. In some embodiments, the control is a negative control sample obtained from a healthy patient. In other embodiments, the control is a positive control sample obtained from a patient diagnosed with RSV infection. In still other embodiments, the control is a historical control or standard reference value or range of values (such as a previously tested control sample, such as a group of RSV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Effective amount: An amount of agent, such as an immunogen, that is sufficient to generate a desired response, such as an immune response in a subject. It is understood that to obtain a protective immune response against an antigen of interest can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to generate a protective immune response. In one example, a desired response is to induce an immune response that inhibits or prevents RSV infection in a subject.

Epitope: An antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on the RSV G protein. Epitopes can be formed both from contiguous amino acids or noncontiguous amino acids juxtaposed by tertiary folding of a protein.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Glycosylation site: An amino acid sequence on the surface of a polypeptide, such as a protein, which accommodates the attachment of a glycan. An N-linked glycosylation site is triplet sequence of NX(S/T) in which N is asparagine, X is any residues except proline, and (S/T) is a serine or threonine residue. A glycan is a polysaccharide or oligosaccharide. Glycan may also be used to refer to the carbohydrate portion of a glycoconjugate, such as a glycoprotein, glycolipid, or a proteoglycan.

Heterologous: Originating from a different genetic source.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). The immune response can elicit innate, antibody, or cellular immunity In one embodiment, an immune response is a T cell response, such as a CD4+ response or a CD8+ response. In another embodiment, the response is a B cell response, and results in the production of specific antibodies.

Immunogen: A compound, composition, or protein (for example, a recombinant RSV G ectodomain) that can elicit an immune response in an animal, including compositions that are injected or absorbed into an animal. Administration of an immunogen to a subject can lead to protective immunity against a pathogen of interest.

Immunogenic composition: A composition comprising a disclosed recombinant RSV G ectodomain that induces a measurable CTL response against the RSV, or induces a measurable B cell response (such as production of antibodies) against the RSV, when administered to a subject. It further refers to isolated nucleic acid molecules and vectors encoding a disclosed recombinant RSV G ectodomain that can be used to express the protein (and thus be used to elicit an immune response against recombinant RSV G ectodomain). For in vivo use, the immunogenic composition will typically include the recombinant RSV G ectodomain or a nucleic acid molecule encoding the recombinant RSV G ectodomain in a pharmaceutically acceptable carrier and may also include other agents, such as an adjuvant.

Inhibiting or treating a disease or condition: Reducing the full development of a disease or condition in a subject, for example, reducing the full development of RSV in a subject who has an RSV infection, and/or reducing RSV infection in a subject or population of subjects at risk thereof. This includes neutralizing, antagonizing, prohibiting, preventing, restraining, slowing, disrupting, stopping, or reversing progression or severity of the disease or condition.

Inhibiting a disease or condition refers to a prophylactic intervention administered before the disease or condition has begun to develop (for example, by vaccinating a subject at risk of RSV infection, but not infected by RSV, with an RSV G ectodomain as disclosed herein) that reduces subsequent development of the disease or condition, and also to amelioration of one or more signs or symptoms of the disease or condition following development. The term "ameliorating," with reference to inhibiting a disease or condition refers to any observable beneficial effect of the intervention intended to inhibit the disease or condition. The beneficial effect can be evidenced, for example, by a delayed onset of clinical symptoms of the disease or condition in a susceptible subject, a reduction in severity of some or all clinical symptoms of the disease or condition, a slower progression of the disease or condition, an improvement in the overall health or well-being of the subject, a reduction in infection, or by other parameters well known in the art that are specific to the particular disease or condition.

In some embodiments, an immune response induced by administering an effective amount of an RSV G ectodomain immunogen as disclosed herein inhibits infection of a human subject by RSV, for example, by at least 50% (such as at least 60%, at least 70%, at least 80%, at least 90%, or more) compared to a suitable control.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and viruses that have been "isolated" include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linker and Linked: A linker is a bi-functional molecule that can be used to link two molecules into one contiguous molecule. Non-limiting examples of peptide linkers include glycine-serine peptide linkers. Unless context indicates otherwise, reference to "linking" a first polypeptide and a second polypeptide, or to two polypeptides "linked" together, or to a first polypeptide having a "linkage" to a second polypeptide, refers to covalent linkage by peptide bond (for example via a peptide linker) such that the first and second polypeptides form a contiguous polypeptide chain. If a peptide linker is involved, the covalent linkage of the first and second polypeptides can be to the N-and C-termini of the peptide linker. Typically, such linkage is accomplished using molecular biology techniques to genetically manipulate DNA encoding the first polypeptide linked to the second polypeptide by the peptide linker.

Native protein or sequence: A polypeptide or sequence that has not been modified, for example, by selective mutation. For example, selective mutation to focus the antigenicity of the antigen to a target epitope. Native protein or native sequence are also referred to as wild-type protein or wild-type sequence.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single-and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as immunogenic compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Prime-boost vaccination: An immunotherapy including administration of a first immunogenic composition (the primer vaccine) followed by administration of a second immunogenic composition (the booster vaccine) to a subject to induce an immune response. The primer vaccine and/or the booster vaccine include a vector (such as a viral vector, RNA, or DNA vector) expressing the antigen to which the immune response is directed. The booster vaccine is administered to the subject after the primer vaccine; the skilled artisan will understand a suitable time interval between administration of the primer vaccine and the booster vaccine, and examples of such timeframes are disclosed herein. In some embodiments, the primer vaccine, the booster vaccine, or both primer vaccine and the booster vaccine additionally include an adjuvant. In one non-limiting example, the primer vaccine is a DNA-based vaccine (or other vaccine based on gene delivery), and the booster vaccine is a protein subunit or protein nanoparticle based vaccine.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Respiratory Syncytial Virus (RSV): An enveloped non-segmented negative-sense single-stranded RNA virus of the family Paramyxoviridae. The RSV genome is ~15,000 nucleotides in length and includes 10 genes encoding 11 proteins, including the glycoproteins SH, G, and F. The F protein mediates fusion, allowing entry of the virus into the cell cytoplasm and also promoting the formation of syncytia. Two antigenic subgroups of human RSV strains have been described, the A and B subgroups, based primarily on differences in the antigenicity of the G glycoprotein. RSV strains for other species are also known, including bovine RSV. Exemplary RSV strain sequences are known to the person of ordinary skill in the art. Further, several models of human RSV infection are available, including model organisms infected with hRSV, as well as model organisms infected with species specific RSV, such as use of bRSV infection in cattle (see, e.g., Bern et al., *Am J. Physiol. Lung Cell Mol. Physiol.*, 301: L148-L156, 2011; and Nam and Kun (Eds.). Respiratory Syncytial Virus: Prevention, Diagnosis and Treatment. Nova Biomedical Nova Science Publisher, 2011; and Cane (Ed.) Respiratory Syncytial Virus. Elsevier Science, 2007.)

RSV attachment glycoprotein (G): An RSV envelope glycoprotein that is a type II membrane protein and facilitates attachment of RSV to host cell membranes.

The RSV G protein is expressed during RSV infection in two forms. One is the full-length transmembrane form (mG), which is expressed on the cell surface and is packaged into the virus particle. The other form is an N-terminally-truncated, secreted form, sG. The full-length G protein (mG) is a type II protein that has an N-terminal cytoplasmic tail (CT, predicted to comprise approximately amino acids 1-37), a hydrophobic transmembrane domain (TM, comprising approximately amino acids 38-66), and an ectodomain (comprising approximately amino acids 67-298). The sG form is relatively is produced by alternative translation initiation at the second AUG codon (M48) in the ORF, whose corresponding position in the protein lies within the TM domain. The N-terminus is then subjected to intracellular proteolytic trimming that creates a new N-terminus at approximately N66.

An exemplary RSV G protein sequence is provided herein as SEQ ID NO: 1. As used herein, RSV G residue positioning is made with reference to the sequence of RSV G from subtype A2 set forth as SEQ ID NO: 1.

RSV Fusion protein (F): An RSV envelope glycoprotein that facilitates fusion of viral and cellular membranes. In nature, the RSV F protein is initially synthesized as a single polypeptide precursor approximately 574 amino acids in length, designated $F_0$. $F_0$ includes an N-terminal signal peptide that directs localization to the endoplasmic reticulum, where the signal peptide (approximately the first 25 residues of $F_0$) is proteolytically cleaved. The remaining $F_0$ residues oligomerize to form a trimer and are proteolytically processed by a cellular protease at two conserved consensus furin cleavage sequences (approximately $F_0$ positions 109 and 136; for example, $RARR_{109}$ (SEQ ID NO: 57, residues 106-109) and $RKRR_{136}$ (SEQ ID NO: 57, residues 133-136) to generate two disulfide-linked fragments, $F_1$ and $F_2$. The smaller of these fragments, F2, originates from the N-terminal portion of the $F_0$ precursor and includes approximately residues 26-109 of $F_0$. The larger of these fragments, $F_1$, includes the C-terminal portion of the $F_0$ precursor (approximately residues 137-574) including an extracellular/lumenal region (residues 137-529), a transmembrane domain (~residues 530-550), and a cytoplasmic tail (~residues 551-574) at the C-terminus. The extracellular portion of the RSV F protein is the RSV F ectodomain, which includes the $F_2$ protein and the $F_1$ ectodomain.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Specifically bind: When referring to the formation of an antibody:antigen protein complex, or a protein:protein complex, refers to a binding reaction which determines the presence of a target protein, peptide, or polysaccharide (for example, a glycoprotein), in the presence of a heterogeneous population of proteins and other biologics. Thus, under designated conditions, a particular antibody or protein binds preferentially to a particular target protein, peptide or polysaccharide and does not bind in a significant amount to other proteins or polysaccharides present in the sample or subject. Specific binding can be determined by methods known in the art. A first protein or antibody specifically binds to a target protein when the interaction has a $K_D$ of less than $10^{-6}$ Molar, such as less than $10^{-7}$ Molar, less than $10^{-8}$ Molar, less than $10^{-9}$, or even less than $10^{-10}$ Molar.

Soluble protein: A protein capable of dissolving in aqueous liquid at room temperature and remaining dissolved. The solubility of a protein may change depending on the concentration of the protein in the water-based liquid, the buffering condition of the liquid, the concentration of other solutes in the liquid, for example salt and protein concentrations, and the heat of the liquid. In some embodiments, a soluble protein is one that dissolves to a concentration of at least 0.001 mg/mg in phosphate buffered saline (pH 7.4) at room temperature and remains dissolved for at least 48 hours.

Subject: Living multi-cellular vertebrate organisms, a category that includes human and non-human mammals. In an example, a subject is a human. In a particular example, the subject is a newborn infant. In an additional example, a subject is selected that is in need of inhibiting of an RSV infection. For example, the subject is either uninfected and at risk of RSV infection or is infected in need of treatment.

Transmembrane domain: An amino acid sequence that inserts into a lipid bilayer, such as the lipid bilayer of a cell or virus or virus-like particle. A transmembrane domain can be used to anchor an antigen to a membrane. In some examples a transmembrane domain is a RSV G transmembrane domain.

Under conditions sufficient for: A phrase that is used to describe any environment that permits a desired activity.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides, or DNA derived from them. A vaccine may include a disclosed immunogen (such as a recombinant RSV G ectodomain or nucleic acid molecule encoding same), a virus, a cell or one or more cellular constituents. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response. In one specific, non-limiting example, a vaccine prevents and/or reduces the severity of the symptoms associated with RSV infection and/or decreases the viral load compared to a control.

Vector: An entity containing a DNA or RNA molecule bearing a promoter(s) that is operationally linked to the coding sequence of an antigen(s) of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) *J. Virol.* 68:4503-4505; Vincente, *J Invertebr Pathol.*, 2011; Schneider-Ohrum and Ross, *Curr. Top. Microbiol. Immunol.*, 354: 53073, 2012).

II. Recombinant RSV G Ectodomains and Fragments Thereof

Recombinant RSV G ectodomain proteins and fragments thereof are disclosed herein that are modified from a native form and shown to induce an immune response that inhibits RSV infection in an animal model. Thus, the disclosed recombinant RSV G ectodomain s and fragments thereof are immunogens and are useful to induce an immune response in a vertebrate animal (such as mammals, for example, humans and cattle) to RSV (for example RSV A, RSV B, or bovine RSV). In several embodiments, the recombinant RSV G ectodomain or fragment thereof is not glycosylated; for example, the RSV G ectodomain or fragment thereof is produced using a bacterial expression system, or is produced in mammalian or insect or yeast cells and subsequently deglycosylated.

In some embodiments, the recombinant RSV G ectodomain can be a soluble protein, for example, for use as a recombinant subunit vaccine. In other embodiments, the recombinant RSV G ectodomain can be membrane anchored, for example, for use in an attenuated virus or virus like particle vaccine. Membrane anchoring can be accomplished, for example, by N-terminal linkage of the recombinant RSV G ectodomain or fragment thereof to a transmembrane domain and optionally a cytoplasmic tail, such as an RSV G transmembrane domain and cytoplasmic tail.

As used herein, RSV G residue positioning is made with reference to the sequence of RSV G from subtype A2 set forth as SEQ ID NO: 1.

In some embodiments, the recombinant RSV G ectodomain includes an amino acid sequence of a native RSV G ectodomain with a deletion of residues 172-186, for example, from subtype A (e.g., A1 or A2), subtype B (e.g., B1 or B2), or bovine RSV, or an amino acid sequence at least 70% (such as at least 80%, at least 90%, at least 95%, at least 96%, at least 97%, at least 98% or at least 99%) identical thereto that has been modified to include the amino acid deletion as discussed herein. For example, the recombinant RSV G ectodomain includes an amino acid sequence of a native RSV G ectodomain with a deletion of residues 172-186, for example, from subtype A (e.g., A1 or A2), subtype B (e.g., B1 or B2), or bovine RSV, or an amino acid sequence at least 90% identical thereto that has been modified to include the amino acid deletion as discussed herein. In some embodiments, the recombinant RSV G ectodomain includes RSV G residues 67-171 linked to RSV G 187-298 by a heterologous peptide linker, where the RSV G sequences are from subtype A (e.g., A1 or A2), subtype B (e.g., B1 or B2), or bovine RSV, or an amino acid sequence at least 70% (such as at least 80%, at least 90%, at least 95%, at least 96%, at least 97%, at least 98% or at least 99%) identical thereto that has been modified to include the amino acid deletion as discussed herein. For example, the recombinant RSV G ectodomain includes RSV G residues 67-171 linked to RSV G 187-298 by a heterologous peptide linker, where the RSV G sequences are from subtype A (e.g., A1 or A2), subtype B (e.g., B1 or B2), or bovine RSV, or an amino acid sequence at least 90% identical thereto that has been modified to include the amino acid deletion as discussed herein. The heterologous peptide linker can be any appropriate peptide linker, such as a glycine-serine linker, for example, GGGGSGGGGS (SEQ ID NO: 5). A non-limiting example of a recombinant RSV G ectodomain from subtype A2 including RSV G residues 67-171 linked to 187-298 by a heterologous peptide linker is provided as SEQ ID NO: 2:

```
HKVTPTTAIIQDATSQIKNTTPTYLTQNPQLGISPSNPSEITSQITTILA
STTPGVKSTLQSTTVKTKNTTTTQTQPSKPTTKQRQNKPPSKPNNDFHFE
VFNFVGGGGSGGGGSKRIPNKKPGKKTTTKPTKKPTLKTTKKDPKPQTTK
SKEVPTTKPTEEPTINTTKTNIITTLLTSNTTGNPELTSQMETFHSTSSE
GNPSPSQVSTTSEYPSQPSSPPNTPRQ
```

A non-limiting example of a recombinant RSV G ectodomain from subtype B1 including RSV G residues 67-171 linked to 187-298 by a heterologous peptide linker is provided as SEQ ID NO: 11:

```
HKVTLTTVTVQTIKNHTEKNITTYLTQVPPERVSSSKQPTTTSPIHTNSA
TTSPNTKSETHHTTAQTKGRTTTSTQTNKPSTKPRLKNPPKKPKDDYHFE
VFNFVGGGGSGGGGSKTIPSNKPKKKPTIKPTNKPTTKTTNKRDPKTPAK
TTKKETTTNPTKKPTLTTTERDTSTSQSTVLDTTTLEHTIQQQSLHSTTP
ENTPNSTQTPTASEPSTSNSTQNTQSHA
```

In some embodiments, the fragment of the RSV G ectodomain includes an amino acid sequence of the N-terminal domain RSV G domain (such as residues 67-163) of a native RSV G, for example, from subtype A (e.g., A1 or A2), subtype B (e.g., B1 or B2), or bovine RSV, or an amino acid sequence at least 70% (such as at least 80%, at least 90%, at least 95%, at least 96%, at least 97%, at least 98% or at least 99%) identical thereto that has been modified to include the amino acid deletion as discussed herein. For example, the fragment of the RSV G ectodomain includes an amino acid sequence of the N-terminal domain RSV G domain (such as residues 67-163) of a native RSV G, for example, from subtype A (e.g., A1 or A2), subtype B (e.g., B1 or B2), or bovine RSV, or an amino acid sequence at least 90% identical thereto that has been modified to include the amino acid deletion as discussed herein. A non-limiting example of a fragment of a recombinant RSV G ectodomain from subtype A2 sequence including RSV G residues 67-163 is provided as SEQ ID NO: 3:

```
HKVTPTTAIIQDATSQIKNTTPTYLTQNPQLGISPSNPSEITSQITTILA
STTPGVKSTLQSTTVKTKNTTTTQTQPSKPTTKQRQNKPPSKPNNDF
```

A non-limiting example of a fragment of a recombinant RSV G ectodomain from subtype B1 sequence including RSV G residues 67-163 is provided as SEQ ID NO: 12:

```
HKVTLTTVTVQTIKNHTEKNITTYLTQVPPERVSSSKQPTTTSPIHTNSA
TTSPNTKSETHHTTAQTKGRTTTSTQTNKPSTKPRLKNPPKKPKDDY
```

In some embodiments, the fragment of the RSV G ectodomain includes an amino acid sequence of the C-terminal domain RSV G domain (such as residues 187-298) of a native RSV G, for example, from subtype A (e.g., A1 or A2), subtype B (e.g., B1 or B2), or bovine RSV, or an amino acid sequence at least 70% (such as at least 80%, at least 90%, at least 95%, at least 96%, at least 97%, at least 98% or at least 99%) identical thereto that has been modified to include the amino acid deletion as discussed herein. For example, the fragment of the RSV G ectodomain includes an amino acid sequence of the C-terminal domain RSV G domain (such as residues 187-298) of a native RSV G, for example, from subtype A (e.g., A1 or A2), subtype B (e.g., B1 or B2), or bovine RSV, or an amino acid sequence at least 90% identical thereto that has been modified to include the amino acid deletion as discussed herein. A non-limiting example of a fragment of a recombinant RSV G ectodomain from subtype A2 sequence including RSV G residues 187-298 is provided as SEQ ID NO: 4:

KRIPNKKPGRKTTTKPTKKPTLKTTKKOPKPQTTKSKEVPTTKPTEEPTI

NTTKTNIITTLLTSNTTGNPELTSQMETFHSTSSEGNPSPSQVSTTSEYP

SQPSSPPNTPRQ

A non-limiting example of a fragment of a recombinant RSV G ectodomain from subtype B1 sequence including RSV G residues 187-298 is provided as SEQ ID NO: 13:

KTIPSNKPKKKPTIKPTNKPTTKTTNKRDPKTPAKTTKKETTTNPTKKPT

LTTTERDTSTSQSTVLDTTTLEHTIQQQSLHSTTPENTPNSTQTPTASEP

STSNSTQNTQSHA

The disclosed recombinant RSV G ectodomain or fragment thereof can be derived from any type of RSV, such as subtype A (e.g., A1 or A2), subtype B (e.g., B1 or B2), or bovine RSV. RSV G proteins from the different RSV subtypes, as well as nucleic acid sequences encoding such proteins and methods for the manipulation and insertion of such nucleic acid sequences into vectors, are known. A non-limiting example of a RSV G protein sequence from subtype A2 is provided as SEQ ID NO: 1:

MSKNKDQRTAKTLERTWDTLNHLLFISSCLYKLNLKSVAQITLSILAMII

STSLIIAAIIFIASANHKVTPTTAIIQDATSQIKNTTPTYLTQNPQLGIS

PSNPSEITSQITTILASTTPGVKSTLQSTTVKTKNTTTTQTQPSKPTTKQ

RQNKPPSKPNNDFHFEVFNFVPCSICSNNPTCWAICKRIPNKKPGKKTTT

KPTKKPTLKTTKKDPKPQTTKSKEVPTTKPTEEPTINTTKTNIITTLLTS

NTTGNPELTSQMETFHSTSSEGNPSPSQVSTTSEYPSQPSSPPNTPRQ

A non-limiting example of a RSV G protein sequence from subtype B1 is provided as SEQ ID NO: 14:

MSKHKNQRTARTLEKTWDTLNHLIVISSCLYRLNLKSIAQIALSVLAMII

STSLIIAAIIFIISANHKVTLTTVTVQTIKNHTEKNITTYLTQVPPERVS

SSKQPTTTSPIHTNSATTSPNTKSETHHTTAQTKGRTTTSTQTNKPSTKP

RLKNPPKKPKDDYHFEVFNFVPCSICGNNQLCKSICKTIPSNKPKKKPTI

KPTNKPTTKTTNKRDPKTPAKTTKKETTTNPTKKPTLTTTERDTSTSQST

VLDTTTLEHTIQQQSLHSTTPENTPNSTQTPTASEPSTSNSTQNTQSHA

The recombinant RSV G ectodomain can comprise modifications of the native RSV G sequence, such as amino acid substitutions, deletions or insertions, glycosylation and/or covalent linkage to unrelated proteins (e.g., a protein tag), as long as the recombinant RSV G ectodomain remains retains immunogenic properties. These variations in sequence can be naturally occurring variations or they can be engineered through the use of genetic engineering techniques. Examples of such techniques are found in see, e.g., Sambrook et al. (Molecular Cloning: A Laboratory Manual, 4$^{th}$ ed., Cold Spring Harbor, New York, 2012) and Ausubel et al. (In Current Protocols in Molecular Biology, John Wiley & Sons, New York, through supplement 104, 2013, both of which are incorporated herein by reference in their entirety.

The recombinant RSV G ectodomain disclosed herein can comprise additional amino acid substitutions that are known to increase the stability or expression of the protein.

In some embodiments, the recombinant RSV G ectodomain can comprise one or more amino acid substitutions compared to a corresponding native RSV G sequence. For example, in some embodiments, the recombinant RSV G ectodomain includes up to 20 (such as up to 1, 2, 3, 4, 5, 6, 7, 8, 9, 10, 11, 12, 13, 14, 15, 16, 17, 18, or 19) amino acid substitutions (such as conservative amino acid substitutions) compared to a native RSV G ectodomain sequence, such the sequence of a RSV G protein set forth as SEQ ID NO: 1, in addition to the deletion of residues 171-186 as discussed herein. The simplest modifications involve the substitution of one or more amino acids for amino acids having similar biochemical properties, such as conservative amino acid substitutions. Such substitutions are likely to have minimal impact on the activity of the resultant protein.

In some embodiments, the recombinant RSV G ectodomain can be joined at either end to other unrelated sequences (for example non-RSV G protein sequences, non-viral envelope, or non-viral protein sequences). The recombinant RSV G ectodomain can be derivatized or linked to another molecule (such as another peptide or protein).

In several embodiments, the recombinant RSV G ectodomain or fragment thereof is soluble in aqueous solution. In some embodiments, the recombinant RSV G ectodomain dissolves to a concentration of at least 0.001 mg/ml (such as at least 0.2 mg/ml, 1.0 mg/ml, 1.5 mg/ml, 2.0 mg/ml, 3.0 mg/ml, 4.0 mg/ml or at least 5.0 mg/ml) in aqueous solution (such as phosphate buffered saline (pH 7.4) or 350 mM NaCl (pH 7.0)) at room temperature (e.g., 20-22 degrees Celsius) and remains dissolved for at least 12 hours (such as at least 24 hours, at least 48 hours, at least one week, at least two weeks, at least one month, or more time). In one embodiment, the phosphate buffered saline includes NaCl (137 mM), KCl (2.7 mM), $Na_2HPO_4$ (10 mM), $KH_2PO_4$ (1.8 mM) at pH 7.4. In some embodiments, the phosphate buffered saline further includes $CaCl_2$ (1 mM) and $MgCl_2$ (0.5 mM). The person of skill in the art is familiar with methods of determining if a protein remains in solution over time. For example, the concentration of the protein dissolved in an aqueous solution can be tested over time using standard methods.

In certain embodiments, the recombinant RSV G ectodomain or fragment thereof may be further modified to contain additional nonproteinaceous moieties that are known in the art and readily available. The moieties suitable for derivatization of the immunogen include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propylene glycol homopolymers, prolypropylene oxide/ ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the immunogen to be improved or altered, whether the immunogen derivative will be used in a therapy under defined conditions, etc.

In some embodiments, the recombinant RSV G ectodomain or fragment thereof can be membrane anchored, for example, for embodiments where the RSV G ectodomain is expressed on an attenuated viral vaccine, or a virus like particle. In such embodiments, the N-terminal residue of the recombinant RSV G ectodomain is linked to a transmembrane domain, and/or a transmembrane domain and cytosolic tail. In some embodiments, one or more peptide linkers (such as a gly-ser linker, for example, a 10 amino acid glycine-serine peptide linker) can be used to link the recombinant RSV G ectodomain to the transmembrane domain.

Non-limiting examples of transmembrane domains for use with the disclosed embodiments include a RSV G transmembrane domain, such as VAQITLSILAMIISTSLIIAAIIFIASAN (SEQ ID NO: 7), the Influenza A Hemagglutinin TM domain (ILAIYSTVASSLVLLVSLGAISF, SEQ ID NO: 8), and the Influenza A Neuraminidase TM domain (IITIGSICMVVGIISLILQIGNIISIWVS, SEQ ID NO: 9). A non-limiting example of a cytosolic tail and transmembrane domain for use with the disclosed embodiments is a RSV G cytosolic tail and transmembrane domain, such as MSKNKDQRTAKTLERTWDTLNHLLFISSCLYKLNLKSVAQITLSILAMIISTSLIIAAIIFIASAN, SEQ ID NO: 10. A non-limiting example of a full length recombinant RSV G from subtype A2 including the deletion of residues 172-186 disclosed herein with residues 171 linked to 187 linked by a heterologous peptide linker is provided as SEQ ID NO: 6:

MSKNKDQRTAKTLERTWDTLNHLLFISSCLYKLNLKSVAQITLSILAMII

STSLIIAAIIFIASANHKVTPTTAIIQDATSQIKNTTPTYLTQNPQLGIS

PSNPSEITSQITTILASTTPGVKSTLQSTTVKTKNTTTTQTQPSKPTTKQ

RQNKPPSKPNNDFHFEVFNFVGGGGSGGGGSKRIPNKKPGKKTTTKPTKK

PTLKTTKKDPKPQTTKSKEVPTTKPTEEPTINTTKTNIITTLLTSNTTGN

PELTSQMETFHSTSSEGNPSPSQVSTTSEYPSQPSSPPNTPRQ

A non-limiting example of a RSV G protein sequence from subtype B1 including the deletion of residues 172-186 disclosed herein with residues 171 linked to 187 linked by a heterologous peptide linker is provided as SEQ ID NO: 15:

MSKHKNQRTARTLEKTWDTLNHLIVISSCLYRLNLKSIAQIALSVLAMII

STSLIIAAIIFIISANHKVTLTTVTVQTIKNHTEKNITTYLTQVPPERVS

SSKQPTTTSPIHTNSATTSPNTKSETHHTTAQTKGRTTTSTQTNKPSTKP

RLKNPPKKPKDDYHFEVFNFVGGGSGGGGSKTIPSNKPKKKPTIKPTNK

-continued
PTTKTTNKRDPKTPAKTTKKETTTNPTKKPTLTTTERDTSTSQSTVLDTT

TLEHTIQQQSLHSTTPENTPNSTQTPTASEPSTSNSTQNTQSHA

III. Polynucleotides and Expression

Polynucleotides encoding a disclosed recombinant RSV G ectodomain or fragment thereof are also provided. These polynucleotides include DNA, cDNA and RNA molecules which encode the recombinant RSV G ectodomain or fragment thereof. The genetic code can be used to construct a variety of functionally equivalent nucleic acids, such as nucleic acids which differ in sequence but which encode the same protein sequence, or encode a conjugate or fusion protein including the nucleic acid sequence.

Exemplary nucleic acid sequences include:

RSV G subtype A2 (1-298) (SEQ ID NO: 16):
ATGTCAAAAAATAAAGACCAACGCACGGCGAAAACCCTGGAACGCACCTG

GGATACCCTGAATCATCTGCTGTTCATCTCCTCCTGCCTGTATAAACTGA

ATCTGAAAAGTGTTGCACAGATTACCCTGTCCATCCTGGCTATGATTATC

AGTACCTCCCTGATTATCGCGGCCATCATCTTCATCGCAAGTGCTAACCA

TAAAGTCACCCCGACCACGGCGATTATCCAGGATGCCACCTCTCAAATCA

AAAACACCACGCCGACGTACCTGACCCAGAATCCGCAACTGGGCATTTCA

CCGTCGAACCCGTCAGAAATCACCTCGCAGATTACCACGATCCTGGCAAG

CACCACGCCGGGTGTCAAAAGCACGCTGCAATCTACCACGGTGAAAACCA

AAAATACCACGACCACGCAGACCCAACCGAGCAAACCGACCACGAAACAG

CGTCAAAATAAACCGCCGTCTAAACCGAACAATGATTTTCACTTCGAAGT

GTTTAACTTCGTTCCGTGCAGTATTTGTTCCAACAATCCGACCTGCTGGG

CCATTTGTAAACGCATCCCGAACAAAAAACCGGGCAAGAAAACCACGACC

AAACCGACGAAAAAACCGACCCTGAAAACGACCAAAAAAGACCCGAAACC

GCAGACGACCAAAAGCAAAGAAGTGCCGACGACCAAACCGACGGAAGAAC

CGACCATTAACACGACCAAAACCAATATTATCACGACCCTGCTGACCTCC

AACACGACCGGCAATCCGGAACTGACCTCACAGATGGAAACGTTCCATTC

GACCAGCTCTGAAGGTAATCCGAGCCCGTCTCAGGTCAGCACGACCTCCG

AATACCCGAGCCAGCCGTCTTCTCCGCCGAATACCCCGCGTCAG

RSV G subtype A2 (1-298 with ΔCCD del-g4s2)
(SEQ ID NO: 17):
ATGTCAAAAAATAAAGACCAACGCACGGCGAAAACCCTGGAACGCACCTG

GGATACCCTGAATCATCTGCTGTTCATCTCCTCCTGCCTGTATAAACTGA

ATCTGAAAAGTGTTGCACAGATTACCCTGTCCATCCTGGCTATGATTATC

AGTACCTCCCTGATTATCGCGGCCATCATCTTCATCGCAAGTGCTAACCA

TAAAGTCACCCCGACCACGGCGATTATCCAGGATGCCACCTCTCAAATCA

AAAACACCACGCCGACGTACCTGACCCAGAATCCGCAACTGGGCATTTCA

CCGTCGAACCCGTCAGAAATCACCTCGCAGATTACCACGATCCTGGCAAG

CACCACGCCGGGTGTCAAAAGCACGCTGCAATCTACCACGGTGAAAACCA

AAAATACCACGACCACGCAGACCCAACCGAGCAAACCGACCACGAAACAG

CGTCAAAATAAACCGCCGTCTAAACCGAACAATGATTTTCACTTCGAAGT

GTTTAACTTCGTTGGTGGTGGCGGCTCCGGTGGCGGTGGTaGcAAACGCA

-continued

TCCCGAACAAAAAACCGGGCAAGAAAACCACGACCAAACCGACGAAAAAA

CCGACCCTGAAAACGACCAAAAAGACCCGAAACCGCAGACGACCAAAAG

CAAAGAAGTGCCGACGACCAAACCGACGGAAGAACCGACCATTAACACGA

CCAAAACCAATATTATCACGACCCTGCTGACCTCCAACACGACCGGCAAT

CCGGAACTGACCTCACAGATGGAAACGTTCCATTCGACCAGCTCTGAAGG

TAATCCGAGCCCGTCTCAGGTCAGCACGACCTCCGAATACCCGAGCCAGC

CGTCTTCTCCGCCGAATACCCCGCGTCAG

RSV G subtype A2 ΔCCD (67-171, g4s2, 187-298)
(SEQ ID NO: 18):
ATGGCGGCCGCACATAAAGTCACCCCGACCACGGCGATTATCCAGGATGC

CACCTCTCAAATCAAAAACACCACGCCGACGTACCTGACCCAGAATCCGC

AACTGGGCATTTCACCGTCGAACCCGTCAGAAATCACCTCGCAGATTACC

ACGATCCTGGCAAGCACCACGCCGGGTGTCAAAAGCACGCTGCAATCTAC

CACGGTGAAAACCAAAAATACCACGACCACGCAGACCCAACCGAGCAAAC

CGACCACGAAACAGCGTCAAAATAAACCGCCGTCTAAACCGAACAATGAT

TTTCACTTCGAAGTGTTTAACTTCGTTGGTGGTGGCGGCTCCGGTGGCGG

TGGTAGCAAACGCATCCCGAACAAAAAACCGGGCAAGAAAACCACGACCA

AACCGACGAAAAAACCGACCCTGAAAACGACCAAAAAAGACCCGAAACCG

CAGACGACCAAAAGCAAAGAAGTGCCGACGACCAAACCGACGGAAGAACC

GACCATTAACACGACCAAAACCAATATTATCACGACCCTGCTGACCTCCA

ACACGACCGGCAATCCGGAACTGACCTCACAGATGGAAACGTTCCATTCG

ACCAGCTCTGAAGGTAATCCGAGCCCGTCTCAGGTCAGCACGACCTCCGA

ATACCCGAGCCAGCCGTCTTCTCCGCCGAATACCCCGCGTCAG

RSV G subtype A2 67-163 (SEQ ID NO: 19):
cATAAAGTCACCCCGACCACGGCGATTATCCAGGATGCCACCTCTCAAAT

CAAAAACACCACGCCGACGTACCTGACCCAGAATCCGCAACTGGGCATTT

CACCGTCGAACCCGTCAGAAATCACCTCGCAGATTACCACGATCCTGGCA

AGCACCACGCCGGGTGTCAAAAGCACGCTGCAATCTACCACGGTGAAAAC

CAAAAATACCACGACCACGCAGACCCAACCGAGCAAACCGACCACGAAAC

AGCGTCAAAATAAACCGCCGTCTAAACCGAACAATGATTTT

RSV G subtype A2 187-298 (SEQ ID NO: 20):
AAACGCATCCCGAACAAAAAACCGGGCAAGAAAACCACGACCAAACCGAC

GAAAAAACCGACCCTGAAAACGACCAAAAAGACCCGAAACCGCAGACGA

CCAAAAGCAAAGAAGTGCCGACGACCAAACCGACGGAAGAACCGACCATT

AACACGACCAAAACCAATATTATCACGACCCTGCTGACCTCCAACACGAC

CGGCAATCCGGAACTGACCTCACAGATGGAAACGTTCCATTCGACCAGCT

CTGAAGGTAATCCGAGCCCGTCTCAGGTCAGCACGACCTCCGAATACCCG

AGCCAGCCGTCTTCTCCGCCGAATACCCCGCGTCAG

RSV G subtype B1 (SEQ ID NO: 21):
ATGTCAAAACACAAAAACCAACGCACCGCCCGCACGCTGGAAAAAACCTG

GGATACGCTGAACCATCTGATTGTCATCTCGTCCTGCCTGTATCGTCTGA

ACCTGAAAAGCATTGCACAAATCGCTCTGTCTGTGCTGGCAATGATTATC

TCCACCTCACTGATTATCGCGGCCATCATCTTCATCATCAGTGCTAACCA

TAAAGTTACCCTGACCACGGTGACGGTTCAGACCATTAAAAACCACACCG

AGAAAAACATCACCACGTACCTGACCCAAGTTCCGCCGGAACGCGTCAGC

TCTAGTAAACAGCCGACCACGACCAGCCCGATTCATACCAACTCAGCGAC

GACCTCGCCGAATACGAAATCTGAAACCCATCACACGACCGCCCAAACCA

AAGGCCGTACGACCACGAGTACGCAGACCAACAAACCGTCCACCAAACCG

CGCCTGAAAAATCCGCCGAAAAAACCGAAAGATGACTATCACTTCGAAGT

CTTTAACTTCGTGCCGTGCAGCATTTGTGGTAACAATCAGCTGTGCAAAT

CAATTTGTAAAACCATCCCGTCGAATAAACCGAAGAAAAAACCGACGATC

AAACCGACCAACAAACCGACCACGAAAACCACGAATAAACGTGATCCGAA

AACCCCGGCAAAAACCACCAAGAAAGAAACCACGACCAACCCGACGAAAA

AACCGACCCTGACGACCACGGAACGCGATACGTCGACCAGCCAATCTACC

GTCCTGGACACCACGACCCTGGAACATACCATTCAGCAACAGAGTCTGCA

CTCCACGACCCCGGAAAACACGCCGAATAGCACCCAGACCCCGACCGCAA

GCGAACCGAGCACCAGCAACTCCACCCAAAACACCCAATCCCACGCA

RSV G subtype B1 Ecoli-Opt, 67-299, SEQ ID NO: 22:
CATAAAGTTACCCTGACCACGGTGACGGTTCAGACCATTAAAAACCACAC

CGAGAAAAACATCACCACGTACCTGACCCAAGTTCCGCCGGAACGCGTCA

GCTCTAGTAAACAGCCGACCACGACCAGCCCGATTCATACCAACTCAGCG

ACGACCTCGCCGAATACGAAATCTGAAACCCATCACACGACCGCCCAAAC

CAAAGGCCGTACGACCACGAGTACGCAGACCAACAAACCGTCCACCAAAC

CGCGCCTGAAAAATCCGCCGAAAAAACCGAAAGATGACTATCACTTCGAA

GTCTTTAACTTCGTGCCGTGCAGCATTTGTGGTAACAATCAGCTGTGCAA

ATCAATTTGTAAAACCATCCCGTCGAATAAACCGAAGAAAAAACCGACGA

TCAAACCGACCAACAAACCGACCACGAAAACCACGAATAAACGTGATCCG

AAAACCCCGGCAAAAACCACCAAGAAAGAAACCACGACCAACCCGACGAA

AAAACCGACCCTGACGACCACGGAACGCGATACGTCGACCAGCCAATCTA

CCGTCCTGGACACCACGACCCTGGAACATACCATTCAGCAACAGAGTCTG

CACTCCACGACCCCGGAAAACACGCCGAATAGCACCCAGACCCCGACCGC

AAGCGAACCGAGCACCAGCAACTCCACCCAAAACACCCAATCCCACGCA

RSV G subtype B1 ΔCCD (1-171, g4s2, 187-298)
(SEQ ID NO: 23):
ATGTCAAAACACAAAAACCAACGCACCGCCCGCACGCTGGAAAAAACCTG

GGATACGCTGAACCATCTGATTGTCATCTCGTCCTGCCTGTATCGTCTGA

ACCTGAAAAGCATTGCACAAATCGCTCTGTCTGTGCTGGCAATGATTATC

TCCACCTCACTGATTATCGCGGCCATCATCTTCATCATCAGTGCTAACCA

TAAAGTTACCCTGACCACGGTGACGGTTCAGACCATTAAAAACCACACCG

AGAAAAACATCACCACGTACCTGACCCAAGTTCCGCCGGAACGCGTCAGC

TCTAGTAAACAGCCGACCACGACCAGCCCGATTCATACCAACTCAGCGAC

GACCTCGCCGAATACGAAATCTGAAACCCATCACACGACCGCCCAAACCA

AAGGCCGTACGACCACGAGTACGCAGACCAACAAACCGTCCACCAAACCG

CGCCTGAAAAATCCGCCGAAAAAACCGAAAGATGACTATCACTTCGAAGT

CTTTAACTTCGTGGGTGGTGGCGGCTCCGGTGGCGGTGGTAGCAAAACCA

```
-continued
TCCCGTCGAATAAACCGAAGAAAAAACCGACGATCAAACCGACCAACAAA

CCGACCACGAAAACCACGAATAAACGTGATCCGAAAACCCCGGCAAAAC

CACCAAGAAAGAAACCACGACCAACCCGACGAAAAAACCGACCCTGACGA

CCACGGAACGCGATACGTCGACCAGCCAATCTACCGTCCTGGACACCACG

ACCCTGGAACATACCATTCAGCAACAGAGTCTGCACTCCACGACCCCGGA

AAACACGCCGAATAGCACCCAGACCCCGACCGCAAGCGAACCGAGCACCA

GCAACTCCACCCAAAACACCCAATCCCACGCA

RSV G subtype B1 Ecoli-Opt, ΔCCD (67-171, g4s2,
187-298) (SEQ ID NO: 24):
CATAAAGTTACCCTGACCACGGTGACGGTTCAGACCATTAAAAACCACAC

CGAGAAAAACATCACCACGTACCTGACCCAAGTTCCGCCGGAACGCGTCA

GCTCTAGTAAACAGCCGACCACGACCAGCCCGATTCATACCAACTCAGCG

ACGACCTCGCCGAATACGAAATCTGAAACCCATCACACGACCGCCCAAAC

CAAAGGCCGTACGACCACGAGTACGCAGACCAACAAACCGTCCACCAAAC

CGCGCCTGAAAAATCCGCCGAAAAAACCGAAAGATGACTATCACTTCGAA

GTCTTTAACTTCGTGGGTGGTGGCGGCTCCGGTGGCGGTGGTAGCAAAAC

CATCCCGTCGAATAAACCGAAGAAAAAACCGACGATCAAACCGACCAACA

AACCGACCACGAAAACCACGAATAAACGTGATCCGAAAACCCCGGCAAAA

ACCACCAAGAAAGAAACCACGACCAACCCGACGAAAAAACCGACCCTGAC

GACCACGGAACGCGATACGTCGACCAGCCAATCTACCGTCCTGGACACCA

CGACCCTGGAACATACCATTCAGCAACAGAGTCTGCACTCCACGACCCCG

GAAAACACGCCGAATAGCACCCAGACCCCGACCGCAAGCGAACCGAGCAC

CAGCAACTCCACCCAAAACACCCAATCCCACGCA
```

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4th ed, Cold Spring Harbor, New York, 2012) and Ausubel et al. (In Current Protocols in Molecular Biology, John Wiley & Sons, New York, through supplement 104, 2013).

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a recombinant RSV G ectodomain or fragment thereof can include a recombinant DNA which is incorporated into a vector (such as an expression vector) into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a recombinant RSV G ectodomain or fragment thereof can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the recombinant RSV G ectodomain or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium,* SF9 cells, C129 cells, 293 cells, Neurospora, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), 4th Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as GnTI$^{-/-}$ cells (ATCC® No. CRL-3022), or HEK-293F cells.

Transformation of a host cell with recombinant DNA can be carried out by conventional techniques. In some embodiments where the host is prokaryotic, such as, but not limited to, *E. coli,* competent cells which are capable of DNA uptake can be prepared from cells harvested after exponential growth phase and subsequently treated by the $CaCl_2$ method. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). Appropriate expression systems such as plasmids and vectors of use in producing proteins in cells including higher eukaryotic cells such as the COS, CHO, HeLa and myeloma cell lines.

In one non-limiting example, a disclosed immunogen is expressed using the pVRC8400 vector (described in Barouch et al., J. Virol., 79, 8828-8834, 2005, which is incorporated by reference herein).

Modifications can be made to a nucleic acid encoding a recombinant RSV G ectodomain or fragment thereof without diminishing its biological activity. Some modifications can be made to facilitate the cloning, expression, or incorporation of the targeting molecule into a fusion protein. Exemplary modifications include termination codons, a methionine added at the amino terminus to provide an initiation, site, additional amino acids placed on either terminus to create conveniently located restriction sites, or additional amino acids (such as poly His) to aid in purification steps.

III. Viral Vectors

A nucleic acid molecule encoding a recombinant RSV G ectodomain or fragment thereof can be included in a viral vector, for example for expression of the recombinant RSV G ectodomain in a host cell, or for immunization of a subject as disclosed herein. In some embodiments, the viral vectors are administered to a subject as part of a prime-boost vaccination. Typically such viral vectors include a nucleic acid molecule encoding a recombinant RSV G ectodomain or fragment thereof that is linked to an N-terminal transmembrane domain, for example the recombinant RSV G ectodomain can be linked to a transmembrane domain and cytosolic tail from a native RSV G protein. In several embodiments, the viral vectors are included in a vaccine, such as a primer vaccine or a booster vaccine for use in a prime-boost vaccination.

In some examples, the viral vector encoding the recombinant RSV G ectodomain or fragment thereof can be replication-competent. For example, the viral vector can have a mutation (e.g., insertion of nucleic acid encoding the recombinant RSV G ectodomain) in the viral genome that attenuates, but does not completely block viral replication in host cells. In several embodiments, the viral vector encoding the recombinant RSV G ectodomain or fragment thereof is a viral vector that can be delivered via the respiratory tract.

Additional viral vectors are also available for expression of the disclosed antigens, including polyoma, i.e., SV40 (Madzak et al., 1992, *J. Gen. Virol.*, 73:15331536), adenovirus (Berkner, 1992, *Cur. Top. Microbiol. Immunol.*, 158: 39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV and CMV (Margolskee, 1992, *Curr. Top. Microbiol. Immunol.*, 158:67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091, 309 and 5,2217,879), alphaviruses (S. Schlesinger, 1993, *Trends Biotechnol.* 11:18-22; I. Frolov et al., 1996, *Proc. Natl. Acad. Sci.* USA 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158: 1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

IV. Virus-Like Particles

In some embodiments, a virus-like particle (VLP) is provided that includes a disclosed recombinant RSV G ectodomain or fragment thereof. Typically such VLPs include a recombinant RSV G ectodomain or fragment thereof that is membrane anchored by an N-terminal transmembrane domain, for example the recombinant RSV G ectodomain or fragment thereof can be linked to a native RSV G transmembrane domain and cytosolic tail. VLPs lack the viral components that are required for virus replication and thus represent a highly attenuated, replication-incompetent form of a virus. However, the VLP can display a polypeptide (e.g., a recombinant RSV G ectodomain or fragment thereof) that is analogous to that expressed on infectious virus particles and can eliciting an immune response to RSV when administered to a subject. Exemplary virus like particles and methods of their production, as well as viral proteins from several viruses that are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rotavirus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Virol. 70: 5422-9 (1996)), hepatitis E virus (Li et al., J. Virol. 71: 7207-13 (1997)), and Newcastle disease virus. The formation of such VLPs can be detected by any suitable technique. Examples of suitable techniques for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

V. Immunogenic Compositions

Immunogenic compositions comprising a disclosed recombinant RSV G ectodomain or fragment thereof or a nucleic acid molecule or vector encoding a recombinant RSV G ectodomain or fragment thereof and a pharmaceutically acceptable carrier are also provided. Such compositions can be administered to subjects by a variety of administration modes known to the person of ordinary skill in the art, for example, intramuscular, subcutaneous, intravenous, intra-arterial, intra-articular, intraperitoneal, or parenteral routes. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995.

Thus, a disclosed recombinant RSV G ectodomain or fragment thereof or a nucleic acid molecule or vector encoding a recombinant RSV G ectodomain or fragment thereof can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance an immune response of the host. Adjuvants, such as aluminum hydroxide (ALHYDROGEL®, available from Brenntag Biosector, Copenhagen, Denmark and Amphogel®, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), TLR agonists (such as TLR-9 agonists), among many other suitable adjuvants well known in the art, can be included in the compositions. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, Ind.) and IL-12 (Genetics Institute, Cambridge, Mass.), among many other suitable adjuvants well known in the art, may be used as an adjuvant (Newman et al., 1998, *Critical Reviews in Therapeutic Drug Carrier Systems* 15:89-142). These adjuvants have the advantage in that they help to stimulate the immune system in a non-specific way, thus enhancing the immune response to a pharmaceutical product.

In several embodiments, the adjuvant is selected to elicit a Th$_1$-biased immune response in a subject.

In some instances, the adjuvant formulation a mineral salt, such as a calcium or aluminum (alum) salt, for example calcium phosphate, aluminum phosphate or aluminum hydroxide. In some embodiments, the adjuvant includes an oil and water emulsion, e.g., an oil-in-water emulsion (such as MF59 (Novartis) or AS03 (GlaxoSmithKline). One example of an oil-in-water emulsion comprises a metabolisable oil, such as squalene, a tocol such as a tocopherol, e.g., alpha-tocopherol, and a surfactant, such as sorbitan trioleate (Span 85) or polyoxyethylene sorbitan monooleate (Tween 80), in an aqueous carrier.

In some instances it may be desirable to combine a disclosed recombinant RSV G ectodomain or fragment thereof or a nucleic acid molecule or vector encoding a recombinant RSV G ectodomain or fragment thereof with other pharmaceutical products (e.g., vaccines) which induce protective responses to other antigens, such as RSV F protein. For example, a composition including a recombinant RSV G protein or fragment thereof as described herein can be can be administered simultaneously or sequentially with other vaccines recommended by the Advisory Committee on Immunization Practices (ACIP; cdc.gov/vaccines/acip/index.html) for the targeted age group (e.g., infants from approximately one to six months of age). As such, the recombinant RSV G ectodomain or fragment thereof or nucleic acid molecule or vector encoding the recombinant RSV G ectodomain or fragment thereof may be administered simultaneously or sequentially with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

In some embodiments, the composition can be provided as a sterile composition. The immunogenic composition typically contains an effective amount of a disclosed recombinant RSV G ectodomain or fragment thereof or a nucleic acid molecule or vector encoding a recombinant RSV G ectodomain or fragment thereof and can be prepared by conventional techniques. Typically, the amount of the recombinant RSV G ectodomain or fragment thereof or nucleic acid molecule or vector encoding the recombinant RSV G ectodomain or fragment thereof in each dose of the immunogenic composition is selected as an amount which induces an immune response without significant, adverse side effects. In some embodiments, the composition can be provided in unit dosage form for use to induce an immune response in a subject, for example, to prevent RSV infection in the subject. A unit dosage form contains a suitable single preselected dosage for administration to a subject, or suitable marked or measured multiples of two or more preselected unit dosages, and/or a metering mechanism for administering the unit dose or multiples thereof.

In some embodiments, the composition includes a first recombinant RSV G ectodomain or fragment thereof that is based on a RSV G subtype A protein, and a second recombinant RSV G ectodomain or fragment thereof that is based on a RSV G subtype B protein.

The composition can include any suitable concentration of the recombinant RSV G protein or fragment thereof. In several embodiments, the composition comprises the recombinant RSV G protein or fragment thereof at a concentration of from 0.5 μg/ml to 5 mg/ml, such as from 0.5 μg/ml to 5 μg/ml, from 1 μg/ml to 2 μg/ml, from 1 μg/ml to 10 μg/ml, from 10 μg/ml to 100 μg/ml, from 100 μg/ml to 1 mg/ml, from 1 μg/ml to 1 mg/ml, or from 1 mg/ml to 5 mg/ml.

VI. Methods of Inducing an Immune Response

The disclosed immunogens (e.g., recombinant RSV G ectodomain, or a nucleic acid molecule (such as an RNA molecule) or vector encoding the recombinant RSV G ectodomain) can be administered to a subject to induce an immune response to RSV G protein in the subject. In a particular example, the subject is a human. The immune response can be a protective immune response, for example a response that inhibits subsequent infection with RSV. In some embodiments, the immune response may not completely protect against subsequent RSV infection, but does reduce (for example, by at least 50%, such as at least 75%) the severity of subsequent infection, particularly in the lower respiratory tract, compared to a non-immunized control. Elicitation of the immune response can also be used to treat or inhibit RSV infection and illnesses associated therewith.

A subject can be selected for treatment that has, or is at risk for developing RSV infection, for example because of exposure or the possibility of exposure to RSV. Following administration of a disclosed immunogen, the subject can be monitored for RSV infection or symptoms associated therewith, or both.

Typical subjects intended for treatment with the immunogens and methods of the present disclosure include humans, as well as non-human primates and other animals, such as cattle. Because nearly all humans are infected with RSV by the age of 5, the entire birth cohort is included as a relevant population for immunization. This could be done, for example, by beginning an immunization regimen anytime from birth to 6 months of age, from 6 months of age to 5 years of age, in pregnant women (or women of childbearing age) to protect their infants by passive transfer of antibody, family members of newborn infants or those still in utero, and subjects greater than 50 years of age. The scope of this disclosure is meant to include maternal immunization. In several embodiments, the subject is a human subject that is seronegative for RSV specific antibodies. In additional embodiments, the subject is no more than one year old, such as no more than 6 months old, no more than 3 months, or no more than 1 month old.

Subjects at greatest risk of RSV infection with severe symptoms (e.g. requiring hospitalization) include children with prematurity, bronchopulmonary dysplasia, and congenital heart disease are most susceptible to severe disease. Atopy or a family history of atopy has also been associated with severe disease in infancy. During childhood and adulthood, disease is milder but can be associated with lower airway disease and is commonly complicated by sinusitis. Disease severity increases in the institutionalized elderly (e.g., humans over 65 years old). Severe disease also occurs in persons with severe combined immunodeficiency disease or following bone marrow or lung transplantation. (See, e.g., Shay et al., JAMA, 282:1440-6, 1999; Hall et al., N Engl J Med. 2009; 360:588-598; Glezen et al., *Am J Dis Child.*, 1986; 140:543-546; and Graham, Immunol. Rev., 239:149-166, 2011, each of which is incorporated by reference herein). Thus, these subjects can be selected for administration of the disclosed immunogens, or a nucleic acid or a viral vector encoding, expressing or including an immunogen.

To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize RSV infection. These and other routine methods allow the clinician to select patients in need of therapy using the methods and immunogenic compositions of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

The administration of a disclosed immunogen can be for prophylactic or therapeutic purpose. When provided prophylactically, the immunogen can be provided in advance of any symptom, for example in advance of infection. The prophylactic administration serves to prevent or ameliorate any subsequent infection. In some embodiments, the methods can involve selecting a subject at risk for contracting RSV infection, and administering a therapeutically effective amount of a disclosed immunogen to the subject. The immunogen can be provided prior to the anticipated exposure to RSV so as to attenuate the anticipated severity, duration or extent of an infection and/or associated disease symptoms, after exposure or suspected exposure to the virus, or after the actual initiation of an infection. When provided therapeutically, the disclosed immunogens are provided at or after the onset of a symptom of RSV infection, or after diagnosis of RSV infection. Treatment of RSV by inhibiting RSV replication or infection can include delaying and/or reducing signs or symptoms of RSV infection in a subject. In some examples, treatment using the methods disclosed herein prolongs the time of survival of the subject.

In some embodiments, administration of a disclosed immunogen to a subject can elicit the production of an immune response that is protective against serious lower respiratory tract disease, such as pneumonia and bronchiolitis, or croup, when the subject is subsequently infected or re-infected with a wild-type RSV. While the naturally circulating virus may still be capable of causing infection, particularly in the upper respiratory tract, there can be a reduced possibility of rhinitis as a result of the vaccination and a possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

The immunogens described herein, and immunogenic compositions thereof, are provided to a subject in an amount effective to induce or enhance an immune response against RSV G protein in the subject, preferably a human. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to RSV proteins. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., inhibition of RSV infection or improvement in disease state (e.g., reduction in viral load). If such monitoring indicates that vaccination is sub-optimal, the subject can be boosted with an additional dose of immunogenic composition, and the vaccination parameters can be modified in a fashion expected to potentiate the immune response.

In some embodiments, the prime administered to the subject includes (or encodes) a disclosed recombinant RSV G ectodomain that is based on a subtype A RSV G protein, and the boost administered to the subject includes (or encodes) a disclosed recombinant RSV G ectodomain that is based on a subtype B RSV G protein. In some embodiments, the prime administered to the subject includes (or encodes) a disclosed recombinant RSV G ectodomain that is based on a subtype B RSV G protein, and the boost administered to the subject includes (or encodes) a disclosed recombinant RSV G ectodomain that is based on a subtype A RSV G protein. In some embodiments, the prime and/or boost compositions administered to the subject each include (or encode) a mixture (such as a 50/50 mixture) of disclosed recombinant RSV G ectodomains that are based on subtype A and subtype B RSV G proteins.

In some embodiments, the prime-boost method can include DNA-primer and protein-boost vaccination protocol to a subject. The method can include two or more administrations of the nucleic acid molecule or the protein.

Each dose administered to a subject will include a suitable amount of the recombinant RSV G ectodomain or fragment thereof. For protein therapeutics, typically, each human dose will comprise 1-2000 µg of protein, such as from about 5 µg to about 2 mg, or from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg. The amount utilized in an immunogenic composition is selected based on the subject population (e.g., infant or elderly). An optimal amount for a particular composition can be ascertained by standard studies involving observation of antibody titers and other responses in subjects. It is understood that a therapeutically effective amount of a disclosed immunogen, such as a recombinant RSV G ectodomain or immunogenic fragment thereof, viral vector, or nucleic acid molecule in a immunogenic composition, can include an amount that is ineffective at eliciting an immune response by administration of a single dose, but that is effective upon administration of multiple dosages, for example in a prime-boost administration protocol.

Upon administration of a disclosed immunogen the immune system of the subject typically responds to the immunogenic composition by producing antibodies specific for viral protein. Such a response signifies that an immunologically effective dose was delivered to the subject.

For each particular subject, specific dosage regimens can be evaluated and adjusted over time according to the individual need and professional judgment of the person administering or supervising the administration of the immunogenic composition. The dosage and number of doses will depend on the setting, for example, in an adult or anyone primed by prior RSV infection or immunization, a single dose may be a sufficient booster. In naive subjects, in some examples, at least two doses would be given, for example, at least three doses. In some embodiments, an annual boost is given, for example, along with an annual influenza vaccination.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, an RSV G protein.

Administration of an immunogenic composition that elicits an immune response to reduce or prevent an infection, can, but does not necessarily completely, eliminate such an infection, so long as the infection is measurably diminished. For example, administration of an effective amount of the agent can decrease the RSV infection (for example, as measured by infection of cells, or by number or percentage of subjects infected by RSV) by a desired amount, for example by at least 10%, at least 20%, at least 50%, at least 60%, at least 70%, at least 80%, at least 90%, at least 95%, at least 98%, or even at least 100% (elimination or prevention of detectable RSV infection, as compared to a suitable control.

In some embodiments, administration of a therapeutically effective amount of one or more of the disclosed immunogens to a subject induces a neutralizing immune response in the subject. To assess neutralization activity, following immunization of a subject, serum can be collected from the subject at appropriate time points, frozen, and stored for neutralization testing. Methods to assay for neutralization activity are known to the person of ordinary skill in the art and are further described herein, and include, but are not limited to, plaque reduction neutralization (PRNT) assays, microneutralization assays, flow cytometry based assays, single-cycle infection assays. In some embodiments, the serum neutralization activity can be assayed using a panel of RSV pseudoviruses.

One approach to administration of nucleic acids is direct immunization with plasmid DNA, such as with a mammalian expression plasmid. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a recombinant RSV G ectodomain can be administered to a subject to induce an immune response to RSV G protein. In some embodiments, the nucleic acid molecule can be included on a plasmid vector for DNA immunization, such as the pVRC8400 vector (described in Barouch et al., J. Virol, 79, 8828-8834, 2005, which is incorporated by reference herein).

In another approach to using nucleic acids for immunization, a disclosed recombinant RSV G ectodomain or immunogenic fragment thereof can also be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

In one embodiment, a nucleic acid encoding a disclosed recombinant RSV G ectodomain or immunogenic fragment thereof, is introduced directly into cells. For example, the nucleic acid can be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

In another embodiment, an mRNA-based immunization protocol can be used to deliver a nucleic acid encoding a disclosed recombinant RSV G ectodomain or fragment thereof directly into cells. In some embodiments, nucleic acid-based vaccines based on mRNA may provide a potent alternative to the previously mentioned approaches. mRNA vaccines preclude safety concerns about DNA integration into the host genome and can be directly translated in the host cell cytoplasm. Moreover, the simple cell-free, in vitro synthesis of RNA avoids the manufacturing complications associated with viral vectors. Two exemplary forms of RNA-based vaccination that can be used to deliver a nucleic acid encoding a disclosed recombinant RSV G ectodomain or fragment thereof include conventional non-amplifying mRNA immunization (see, e.g., Petsch et al., "Protective efficacy of in vitro synthesized, specific mRNA vaccines against influenza A virus infection," Nature biotechnology, 30(12):1210-6, 2012) and self-amplifying mRNA immunization (see, e.g., Geall et al., "Nonviral delivery of self-amplifying RNA vaccines," PNAS, 109(36): 14604-14609, 2012; Magini et al., "Self-Amplifying mRNA Vaccines Expressing Multiple Conserved Influenza Antigens Confer Protection against Homologous and Heterosubtypic Viral Challenge," PLoS One, 11(8):e0161193, 2016; and Brito et al., "Self-amplifying mRNA vaccines," Adv Genet., 89:179-233, 2015).

EXAMPLES

The following examples are provided to illustrate particular features of certain embodiments, but the scope of the claims should not be limited to those features exemplified.

Example 1

Antigenic Sites of RSV G Protein for Inducing a Protective Immune Response

The example describes the immunogenicity in rabbits and mice of recombinant RSV G-ectodomain deleted of the central conserved domain (CCD), as well as G-subdomains (N-and C-terminus), and G-derived short peptides. Evidence is provided showing that that animals vaccinated with the CCD-deleted G-ectodomain, G-subdomains and relevant G peptides had significantly lower viral loads after RSV challenge that correlated with virion binding antibody titers.
Introduction RSV isolates can be classified into two antigenically distinct groups (A and B) with genetic differences occurring mostly in the attachment glycoprotein G (47% heterogeneity at the amino acid level) and to a lesser degree in the fusion protein F (9%) (Mufson et al., J Gen Virol. 1985; 66 (Pt 10):2111-24). In addition, continuous evolution of RSV generates diversity primarily in the G gene (Cane and Pringle, J Virol. 1995; 69(5):2918-25; Tan et al., PLoS One. 2012; 7(12):e51439). Heterologous RSV strains are the main cause of re-infections, and homologous RSV strains are observed less frequently (Collins and Melero, Virus Res. 2011; 162(1-2):80-99; Agoti et al., J Infect Dis. 2012; 206(10):1532-41). However, while there are instances of evolution, e.g. the RSVs with duplications in the G gene, there are also cases of same genotype reappearing over many years. Even though F specific antibodies have been reported to contribute to majority of virus neutralization measure in vitro PRNT assays, the relative contribution of F and G specific antibodies to protection in vivo is not completely understood.

In this example, the immunogenicity of the G-ectodomain lacking part of the central conserved domain (CCD) and the cysteine noose was evaluated, as were individual G-subdomains (N- and C-termini), and G-derived peptides previously identified using GFPDL analysis of post-RSV infection infant sera by immunization of rabbits and mice using virus plaque reduction neutralization test (PRNT), several binding assays including recombinant mammalian cell produced G ectodomain RMG), RSV A2 virions, and recombinant CX3CR1 competition assay. The protective efficacy of these antigenic sites was determined in mouse challenge studies with RSV-A2 line 19F expressing firefly luciferase [rRSV-A2-L19-FFL]. Viral loads in the nasal cavity and lungs were inferred using fluorescence measurements obtained via whole body live imaging as previously described (Fuentes et al., Vaccine. 2017; 35(4):694-702) in addition to plaque forming units (PFU) in the lungs. It was found that animals vaccinated with REGΔCCD, G-subdomains, and G-peptides had significantly lower viral loads after RSV challenge than unimmunized controls. Lung viral loads inversely correlated with RSV A2 virion binding antibody titers (but not with in vitro neutralization titers). Low lung pathology and low Th2/Th1 cytokine ratios was observed in all vaccinated-challenged groups. Therefore, several antigenic sites apart from the CCD motif in the G protein provide protective immunity against RSV.

Results

Figure 1B:
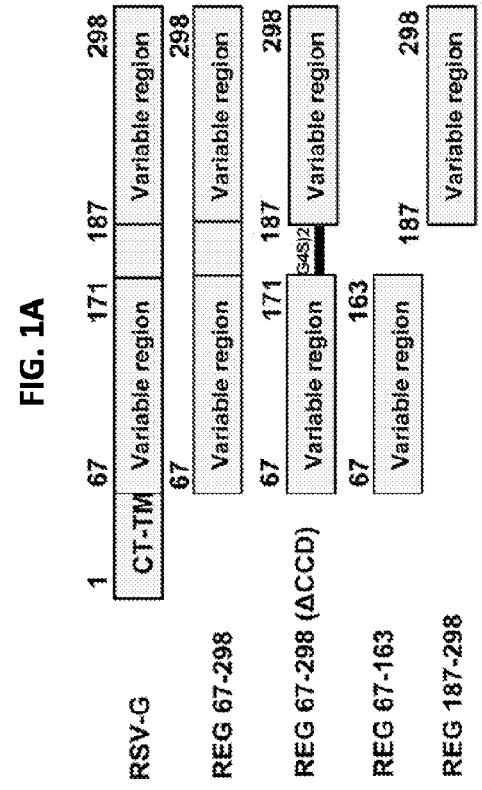
Figure 1C:
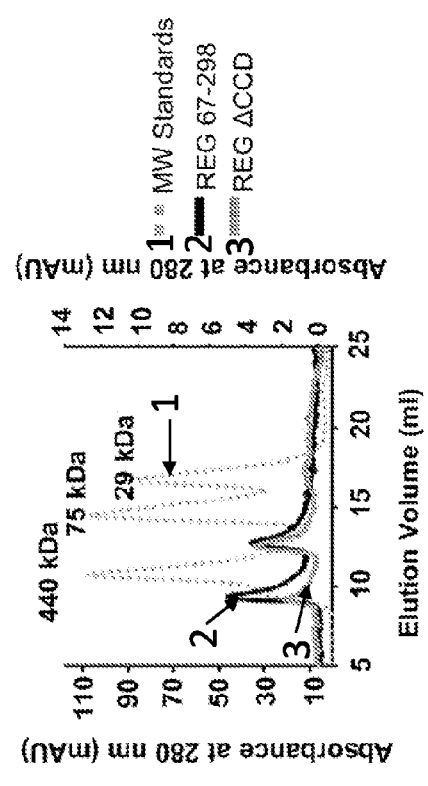
Figure 1D:
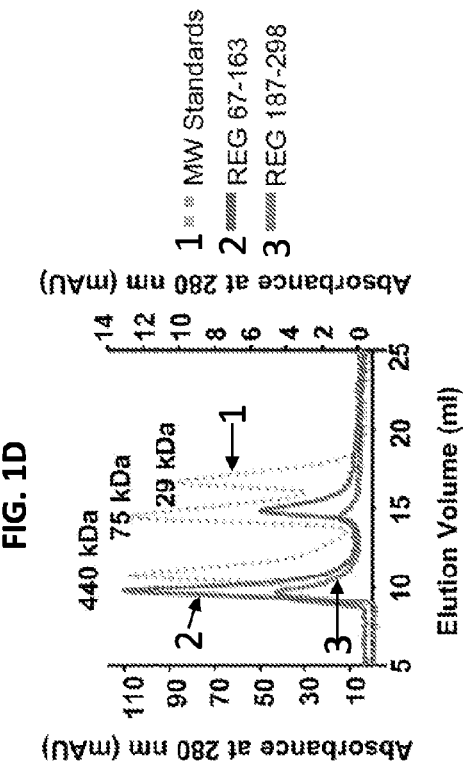

Generation of CCD deleted RSV G protein and G-subdomains in $E.\ coli$. Earlier findings with post primary infection in plasma from infants demonstrated very broad epitope repertoire spanning the entire G ectodomain. In the current study, the contributions of antigenic regions outside of the conserved central domain (CCD; aa residues 172-186) of G to RSV-specific immunity were investigated. As a comparator, a G-ectodomain protein (residues 67-298) of RSV-A2 containing the CCD motif produced using $E.\ coli$ (REG 67-298), which was previously found to generate protective immunity in mice and cotton rats (Fuentes et al., J Virol. 2015; 89(16):8193-205; Fuentes et al., Sci Rep. 2017; 7:42428), was used. The immunogenicity of a CCD-deleted G-ectodomain [REG ΔCCD; with residues 172-186 replaced by a (Gly4Ser)2 linker], and two large G subdomains covering the N-terminus (REG 67-163) and C-terminus (REG 187-298) upstream and downstream of the CCD, respectively, that were identified as immunodominant in the epitope profiling of post-RSV primary infection human sera (FIGS. 1A and 1B). Size exclusion chromatography (SEC) profiles of the four REG proteins using Superdex 200 gel filtration are illustrated in FIGS. 1C-1D. All recombinant G proteins ran as two distinct peaks likely representing tetramers and higher molecular weight oligomers.

CCD is required for in vitro neutralization antibody response following rabbit immunization. Rabbits were immunized three times intramuscularly (i.m.) with 100 μg of purified REG protein combined with Emulsigen adjuvant, bled 8 days after each immunization, and sera evaluated in plaque reduction neutralization assay (PRNT) in the presence of guinea pig complement (GPC). GPC was added to increase the sensitivity of the neutralization assay, as previously we have shown that GPC specifically promotes RSV-A2 virus neutralization by anti-G but not anti-F specific antibodies in vitro (Fuentes et al., Vaccine. 2013; 31 (37):3987-94). As expected, the intact ectodomain (REG 67-298) was highly immunogenic, with peak neutralization titers measured after the second vaccination (FIG. 1E). The REG ΔCCD and the two large fragments elicited modest or low neutralization titers after the second or third vaccinations, respectively (FIG. 1E).

Since in vitro PRNT assays may not detect all antibodies, the binding of immune sera (post-third vaccination) to fully glycosylated G protein from RSV-A2 strain produced in mammalian 293 cells (RMG-A2) was also evaluated (see Fuentes et al., J Virol. 2015; 89(16):8193-205 for RMG-A2 production). All four recombinant proteins generated antibodies in rabbits that bound to fully glycosylated G protein (FIG. 1F). The REG 67-298 immune sera demonstrated the highest peak binding (2,500 RU), followed by REG ΔCCD immune sera (1,600 RU), and by the immune sera generated against the N-terminal and C-terminal domains. The hierarchy of binding to the glycosylated G recapitulated the PRNT virus neutralization titers for the same sera. These findings suggested that while the CCD region is key for generation of measurable neutralizing antibodies in the PRNT assay, there are immunological targets outside the CCD that elicit antibodies that can bind to the fully glycosylated G attachment protein.

Murine challenge studies demonstrate protective efficacy of antigenic regions apart from CCD. Mice were immunized intramuscularly (i.m.) at day 0 and day 20 with 20 μg of purified REG proteins combined with Emulsigen adjuvant. Blood was collected from the tail vein on days 0, 14, and 30. On day 34, mice were inoculated intranasally (i.n.) with $10^6$ PFU of RSV rA2-Line19F-FFL containing homologous RSV-A2 G protein sequence identical to the immunizing REG protein (Fuentes et al., Vaccine. 2017; 35(4):694-702) (FIG. 2A). Previously, the applicability of live imaging was shown for following RSV replication and dissemination from the nasal cavity to the lungs, with a strong correlation between bioluminescence flux units and viral loads measurements by PFU in the lungs of infected animals (Fuentes et al., Vaccine. 2017; 35(4):694-702). All animals vaccinated with REG 67-298 (intact G-ectodomain) completely controlled virus replication in the lung as measured by either live imaging (FIG. 2B) or plaque assay (FIG. 2C) compared to sham (PBS) vaccinated animals. Surprisingly, most the animals immunized twice with REG ΔCCD were also capable of controlling virus replication in the lungs by day 5 post-challenge (FIGS. 2B and 2C). Unexpectedly, some of the animals immunized with the N-terminus REG 67-163, or the C-terminus REG 187-298 also showed significant protection against viral replication in lungs as determined by either Flux or PFU measurements (FIGS. 2B and 2C). In addition to lungs, the live imaging allowed us to measure viral loads in the nasal cavities. All groups of vaccinated animals showed significant reduction in nasal viral loads compared with the PBS control group (FIG. 2D).

Figure 2E:
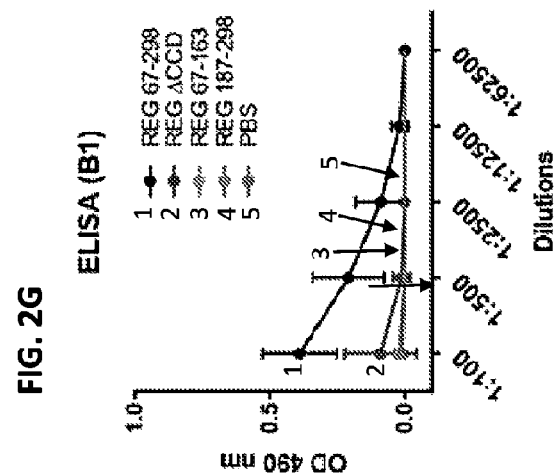
Figure 2F:
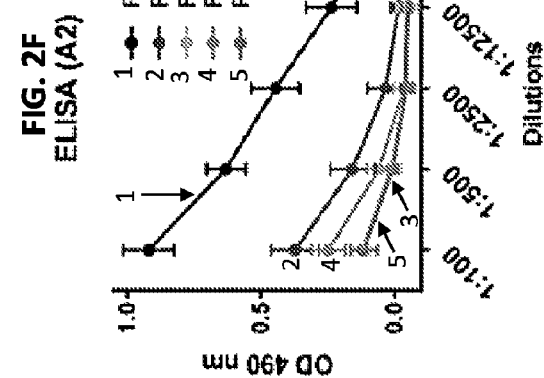
Figure 2G:
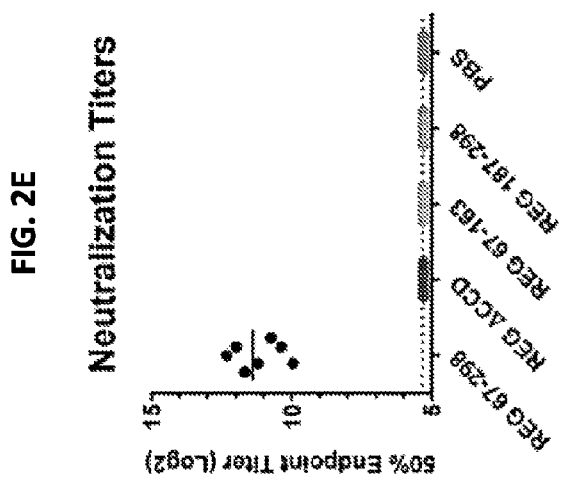

In search for correlates of protection, the immune sera (pre-challenge) was evaluated in virus neutralization and virus particle-binding ELISA. Only sera from mice vaccinated with the entire G-ectodomain (REG 67-298) had detectable virus neutralization activity in vitro (FIG. 2E). As such, the mechanism of protection was not apparent for the REG proteins without CCD and for the N-and C-domains. Several anti-G specific MAbs including 131-2G have been defined that do not neutralize in classical A549 based virus neutralization assay however provide significant protection in animal challenge studies (Haynes et al., J Infect Dis. 2009; 200(3):439-47; Cortjens et al., J Virol. 2017; 91(10)). Therefore, total antibody binding to RSV particles was evaluated by ELISA. Earlier studies confirmed that the virus ELISA express relevant protective epitopes (including conformational epitopes) and can capture monoclonal and polyclonal antibodies with protective titers. However, it is possible that coating of virus particles (virions) on microtiter plates in ELISA may not accurately represent some aspects of structurally intact virions. Antibody binding to RSV A2 virions was highest in immune sera from animals vaccinated with the entire RSV-G ectodomain (REG 67-298) (FIG. 2F). However, some binding to virus particles was also observed with sera from REG ΔCCD, and to a lesser degree with sera from animals vaccinated with the C-terminus domain (REG 187-298) and even weaker binding with sera from the N-terminal domain immunized mice (REG 67-163). The binding antibody endpoint titers to RSV A2 virions are shown in FIG. 2H. We also measured binding to RSV B1 virion particles. As expected, sera from REG 67-298 vaccinated animals bound RSV B1 virions in ELISA although to a lower level compared to RSV-A2 virions, in agreement with our earlier study (Fuentes et al., J Virol. 2015; 89(16): 8193-205) (FIG. 2G). In contrast, the sera from the other three groups did not show significant binding to RSV B1 virions.

On day 5 post-challenge, the viral loads (as measured by plaque assay) in the lungs (FIG. 2C) and nasal cavity (measured by live imaging) (FIG. 2D) inversely correlated with virion binding antibody endpoint titers (FIGS. 2I and 2J) (r=−0.5622 and r=−0.4043, respectively) that reached statistical significance for the lungs (p<0.0152). The results show that in vivo challenge studies are more sensitive than in vitro assays for detection of protective activity of RSV G targeting immune mechanisms.

Figure 3E:
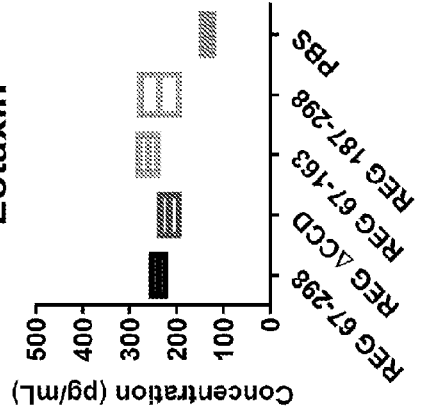
Figure 3F:
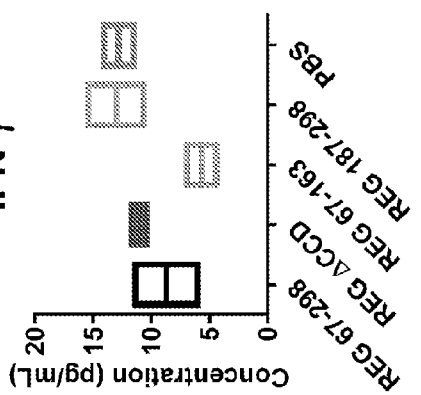
Figure 3G:
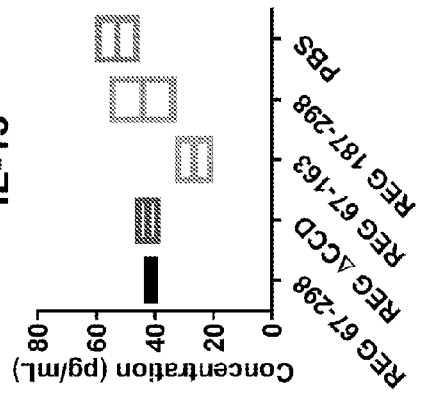
Figure 3H:
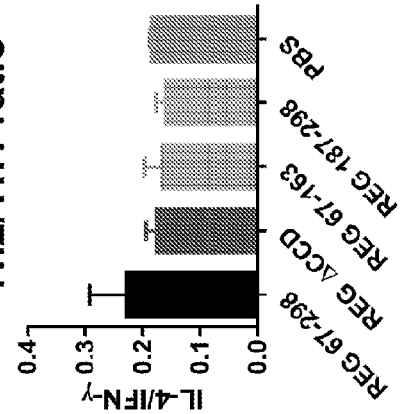
Figure 3I:
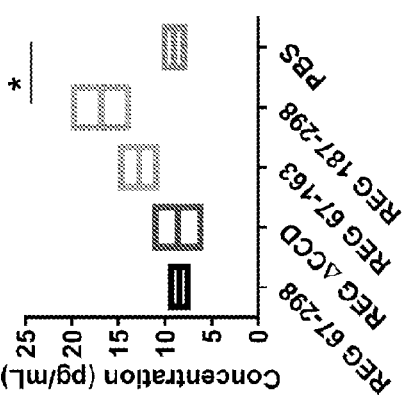
Figure 3J:
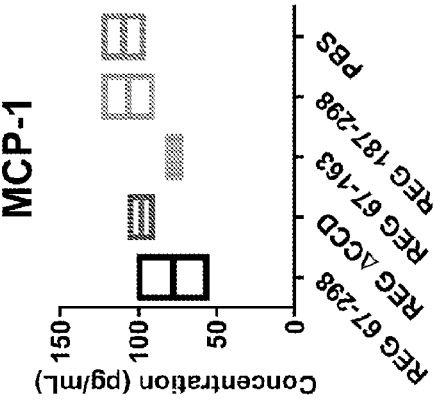

In addition to viral loads, lung pathology (bronchiolitis, perivasculitis, interstitial pneumonia, and alveolitis) was evaluated for all mice on day 5 post-RSV challenge (FIG. 3A). The histology scores for vaccinated animals were not significantly different from the sham vaccinated (PBS) control group. To further explore the possibility of perturbation to the local cytokine milieu, the lung extracts were tested against a cytokines/chemokines multiplex panel (FIGS. 3B and 3I). Levels of most cytokines/chemokines were similar between the vaccinated animals and were not significantly different from the sham vaccinated (PBS) control group following RSV challenge. However, a non-significant elevation of Eotaxin in the vaccinated groups was observed compared with the control group (FIG. 3G), and an elevated MIP-1α levels in the group vaccinated with the C-terminus antigenic domain (REG 187-298) (FIG. 3I). But there were no significant differences in the levels of Th1 and Th2 cytokines and the Th2/Th1 ratio (FIG. 3J) (Fuentes et al., J Virol. 2015; 89(16):8193-205).

Figure 4A:
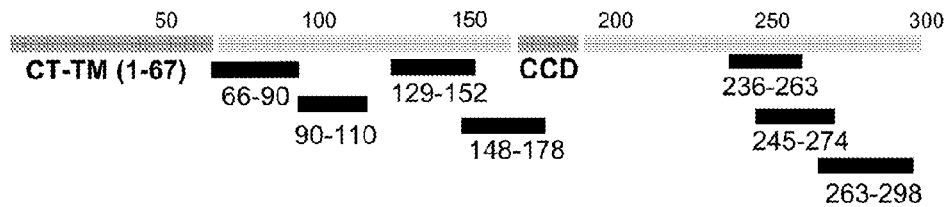
FIGS. 4A-4C. Immunization of rabbits with RSV G peptides.
Figure 4B:
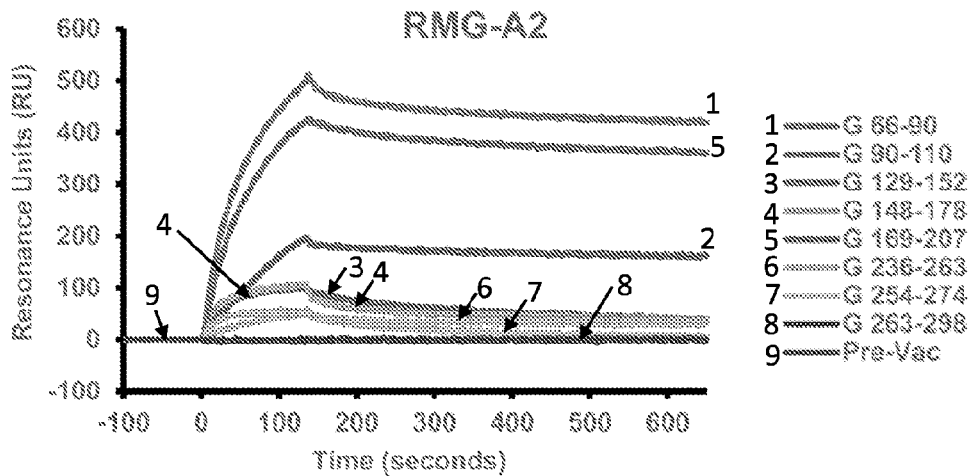
Figure 4C:
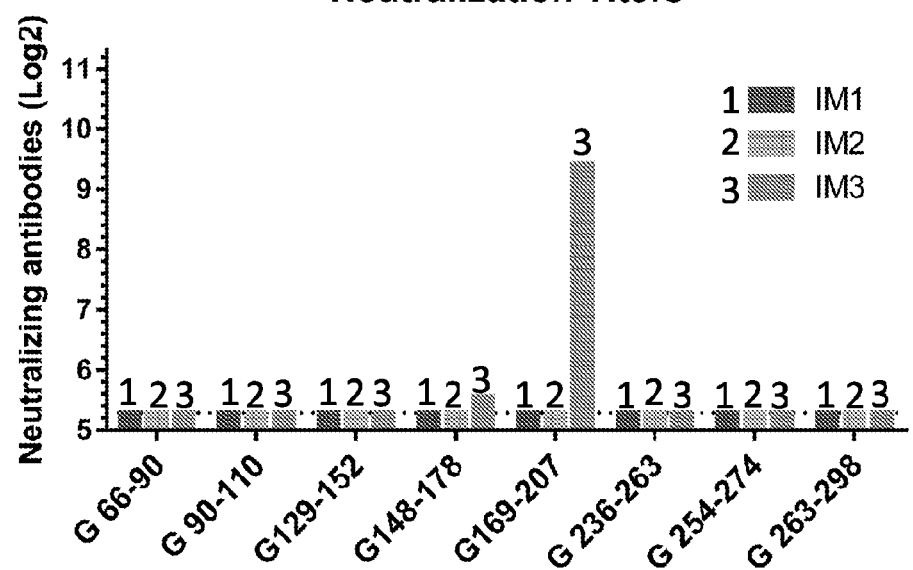

Immunization of rabbits and mice with short antigenic site peptides derived from the N-and C-termini of G-ectodomain. Next peptides were synthesized representing linear antigenic sites that were identified in human post-primary RSV infection in infants (Fuentes et al., PLoS Pathog. 2016; 12(4):e1005554). These peptides were conjugated to KLH and mixed with Emulsigen for vaccination of rabbits and mice (FIG. 4A). The rabbit polyclonal sera obtained after two peptide vaccine doses bound to glycosylated RMG protein in SPR. However, antibody binding titers were 3 to 10-fold lower than antibody binding observed following immunization with REG ΔCCD (FIG. 4B vs. FIG. 1F). Interestingly, the peptide that elicited the highest RMG-binding titer was found in rabbits immunized with the N-terminal G peptide (aa 66-90). However, only peptide G169-207 that overlapped the CCD region elicited neutralizing antibodies after three immunizations (FIG. 4C).

Figure 5A:
Figure 5B:
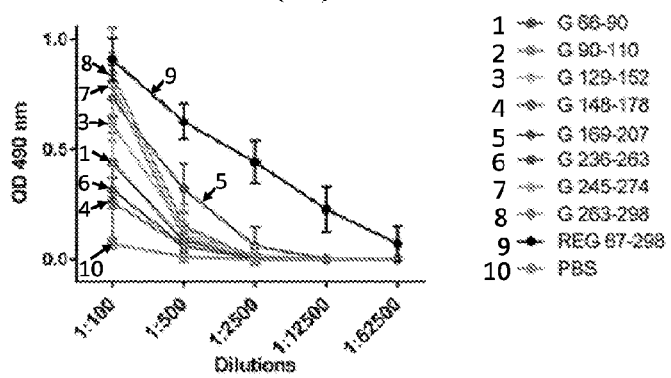
Figure 5C:
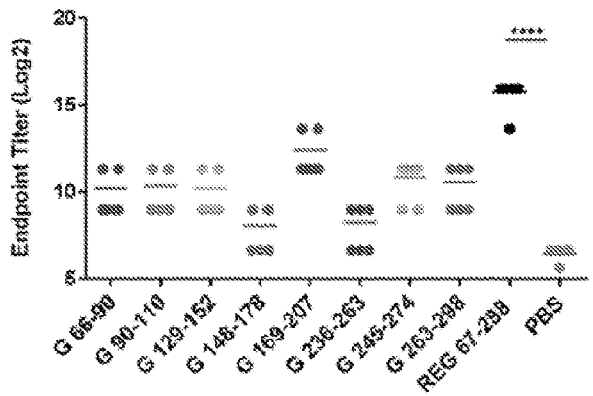
Figure 5G:
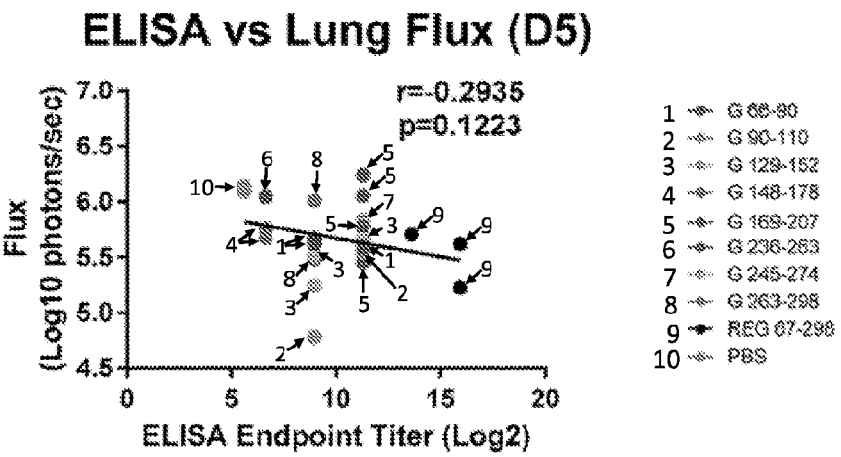
Figure 5H:
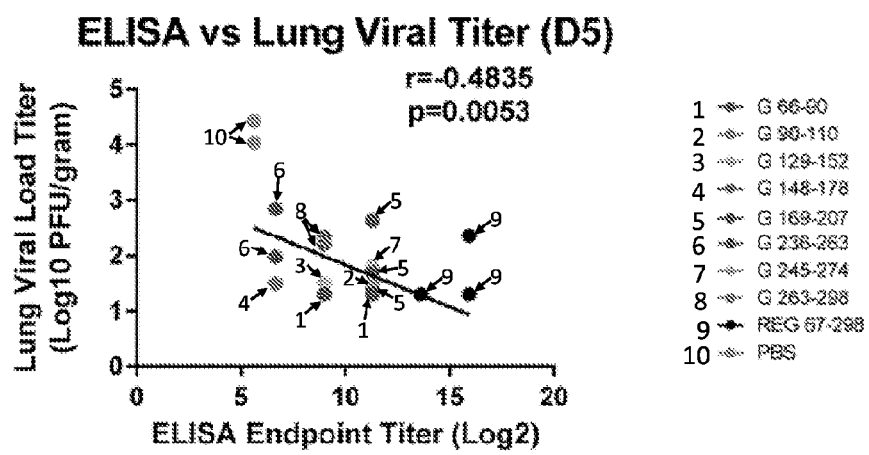
Figure 5I:
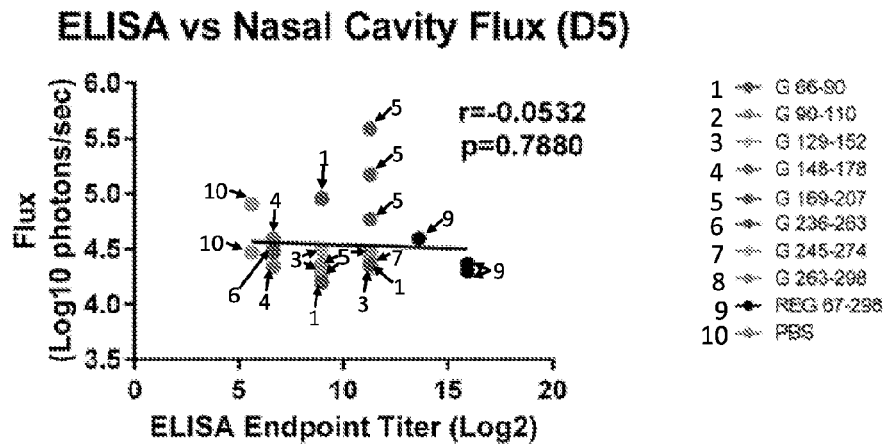

Murine immunization with KLH-conjugated G peptides (FIG. 5A) elicited antibodies that bound RSV A2 virions at various levels, but did not reach the binding titers elicited by the REG 67-298 ectodomain (FIGS. 5B and 5C) (Anderson et al., J Virol. 1988; 62(11):4232-8). Interestingly, following challenge with RSV rA2-Line19F-FFL, the majority of immunized animals showed reduced viral loads in the lungs on day 5 compared with sham-vaccinated animals as measured by either Fluxes (FIG. 5D) or PFU (FIG. 5E). The reduction in lung viral loads measured using live imaging ranged between 40-78% of the sham (PBS vaccinated) control group, and reached statistical significance for most groups of immunized animals, apart from animals immunized with CCD peptide G 169-207 or the G 236-263 peptide (FIG. 5D), suggesting less consistent control of virus replication after challenge in these two peptides vaccinated groups. However, in the PFU assay, all vaccinated groups had statistically lower viral loads compared with the control group (FIG. 5E). The viral loads in the nasal cavity were similar between the control and vaccinated groups, but two animals in the group vaccinated with G 169-207 had elevated fluxes (FIG. 5F). These were the same animals that also had elevated lung fluxes (FIG. 5D), suggesting less consistent control of virus replication after challenge in this specific group. Correlation of the binding antibody ELISA end-point titers to RSV A2 virions with the viral load measurements in the lungs and nasal cavities (FIGS. 5G and 5I) demonstrated significant inverse correlation only between ELISA endpoint titers and the lung viral loads measured in the plaque assay (FIG. 5H, r=−0.4835, p=0.0053).

In the same study, lung sections were evaluated for histopathology (FIG. 6A) at day 5 post-viral challenge. The only notable finding was an increased bronchiolitis score in animals following RSV challenge that were vaccinated with G peptide 169-207, and to a lesser degree in some of the animals vaccinated with G peptide 66-90. Cytokine/chemokine profiling (FIGS. 6B and 6I) revealed significantly higher levels of eotaxin in the lung extracts from the same two (G 66-90 and G 169-207) groups (FIG. 6G). In addition, the Th2/Th1 cytokine ratio was 1 for the G 66-90 peptide vaccinated group, but well below 0.5 for all other vaccinated groups following RSV challenge (FIG. 6J).

Blocking of interaction between RSV G and CX3CR1 receptor by serum antibodies generated in rabbits against different G antigenic domains. Since the in vitro neutralization assay does not reflect infection of human bronchoepithelial cells, which involves interaction between the RSV G protein and surface CX3CR1 (Tripp et al., Nat Immunol. 2001; 2(8):732-8; Jeong et al., PLoS One. 2015; 10(6): e0130517), an SPR-based assay was performed to measure direct antibody-mediated blocking of recombinant CX3CR1 binding to glycosylated G protein produced in 293T cells (RMG) (FIG. 7A). To that end, rabbit pre-vaccination and post 2nd boost sera (at 10-fold dilution) were run on the chip captured with RMG prior to addition of rCXC3R1, and % inhibition was calculated for each serum sample. In this real-time binding assay, the strongest inhibition (90%) of CX3CR1-RMG interaction was observed with antibodies against complete REG ectodomain (67-298) followed by G 169-207 (85%), both of which contain the CX3C motif required for CX3CR1 binding (Tripp et al., Nat Immunol. 2001; 2(8):732-8). Importantly, polyclonal antibodies elicited by the REG ΔCCD (aa 172-186 deleted), inhibited CX3CR1-RMG binding by 70%. In addition, short peptide (G 148-178) and the C-terminal antigenic domain (187-298) inhibited CX3CR1 binding by 48% and 55%, respectively (FIG. 7A).

The degrees of conservation of the individual peptides used in this study among RSV A and RSV B strains was assessed. The percentage homology was high among all RSV A strains but dropped significantly for RSV B strains. However, RSV A2 G peptides aa148-178 and aa169-207 showed ~70% conservation with RSV B1 and circulating B strains. Therefore, a G based protective vaccine may require a combination of G proteins from diverse RSV strains to protect against all RSV strains.

This study demonstrated that in addition to the central conserved domain (CCD) (aa 164-176), there are several protective antigenic sites within RSV-G, including the G-derived N-and C-sub-domains and linear peptides that were recognized by post-RSV infection human sera as previously reported (Fuentes et al., PLoS Pathog. 2016; 12(4): e1005554). Vaccination with these recombinant proteins and peptides provided at least partial protection in mice as measured by reduced lung viral loads on day 5 post challenge with RSV-A2 virus, with no significant lung pathology (FIG. 7B).

Discussion

The G protein undergoes constant diversification in circulating RSV strains, and may contribute to the ability of the virus to reinfect throughout life (Mufson et al., J Gen Virol. 1985; 66 (Pt 10):2111-24; Tan et al., PLoS One. 2012; 7(12):e51439). Several monoclonal antibodies targeting the G protein were demonstrated to have protective activity against severe disease in animal models as well as anti-inflammatory effects (Haynes et al., J Infect Dis. 2009; 200(3):439-47; Collarini et al., J Immunol. 2009; 183(10): 6338-45; Jones et al., PLoS Pathog. 2018; 14(3):e1006935). These MAbs bound to either linear or conformational epitopes overlapping and surrounding the CCD/cysteine noose CX3CR1 binding regions. Furthermore, levels of anti-G antibodies, in addition to antibodies against pre-F, were associated inversely with disease severity in RSV-infected infants and young children (<2yr) (Capella et al., J Infect Dis. 2017; 216(11):1398-406). Therefore, dissecting the immune response to the G protein is important for better understanding of RSV viral immunity and the design of RSV G based vaccines (Tripp et al., J Virol. 2018; 92(3)). In an earlier study, F-and G-phage display libraries (RSV-GFPDL) were used to dissect the antibody repertoire prior to and following primary RSV infection in infants. This analysis identified a large number of epitopes spanning the entire G ectodomain (Fuentes et al., PLoS Pathog. 2016; 12(4): e1005554). In this example, the ability of these linear and conformational antigenic sites within the RSV G attachment protein were evaluated for their immunogenicity and ability to elicit protective immunity against RSV.

To address the contribution of G-CCD for protection against RSV, immunogenicity of full length recombinant RSV-G protein with and without the central conserved domain (CCD) (aa 172-186) was assessed in rabbits and mice. While virus-neutralizing antibody response to the CCD-deleted protein was significantly lower compared with the intact ectodomain, both proteins significantly protected mice from RSV challenge as measured by reduced viral loads in the lungs and nasal cavity. Lung viral loads were inversely correlated with ELISA titers of binding antibodies to RSV A2 virion particles. Furthermore, a low pathology score and very low Th2/Th1 cytokine ratio was measured in the lungs of vaccinated animals on day 5 post RSV challenge, not significantly different from the sham-vaccinated control animals (FIG. 3), suggesting avoidance of the severe lung pathology caused by FI-RSV vaccination (Boyoglu-Barnum et al., J Virol. 2017; 91(10)).

It was previously shown that the CX3C motif downstream of CCD interacts with the CX3CR1 that serves as a receptor for RSV G protein on primary human airway epithelial cells (Johnson et al., PLoS Pathog. 2015; 11(12):e1005318). Several MAbs targeting the CCD motif as well as MAbs 131-2G that binds to a motif upstream of the CCD were shown to block this interaction and neutralize RSV infection of airway broncho-epithelial cells, but not in traditional plaque neutralization assays (Cortjens et al., J Virol. 2017; 91(10); Johnson et al., PLoS Pathog. 2015; 11(12): e1005318; Jeong et al., PLoS One. 2015; 10(6):e0130517; Collarini et al., J Immunol. 2009; 183(10):6338-45) and to protect mice from RSV challenge (Haynes et al., J Infect Dis. 2009; 200(3):439-47; Taylor, Vaccine. 2017; 35(3):469-80). In agreement, the antibodies generated against REG ΔCCD [with CCD residues 172-186 replaced by a (Gly4Ser)$_2$ linker] in the current study, did not demonstrate significant virus neutralization in vitro, but provided significant in vivo protection.

The immunogenicity of N-and C-subdomains of RSV-G and linear G antigenic sites that were identified by GFPDL screening of post-RSV exposure infant sera (Fuentes et al., PLoS Pathog. 2016; 12(4):e1005554) was also assessed. It was found that the N-and C-subdomains (aa 67-163 and aa187-298) flanking the CCD motif generated antibodies that bound to fully glycosylated recombinant G protein produced in mammalian cells (RMG) using SPR, as well as to RSV virions in ELISA, but did not neutralize the virus in a PRNT assay. However, after RSV intranasal challenge of vaccinated mice, partial protection (i.e. reduction in lung and nasal virus loads on day 5) was observed (FIG. 2). Furthermore, synthetic G-peptides containing mostly non-conformational antigenic sites, upstream and downstream of the CCD, also generated antibodies that bound RMG (Fuentes et al., J Virol. 2015; 89(16):8193-205) as well as intact RSV virions in ELISA (FIGS. 2 and 5). Since RMG protein and G protein expressed on RSV virion particles (propagated in mammalian cells) are highly glycosylated, the antigenic sites outside the CCD are expected to be shielded from antibody recognition. Yet RSV-infected children clearly generated antibodies covering both conserved and less conserved sites in the G protein irrespective of predicted glycosylation levels, that could bind to the fully glycosylated G protein on virus particles as shown in our previous study (Fuentes et al., PLoS Pathog. 2016; 12(4):e1005554). Importantly, most animals in the challenge studies demonstrated mild lung pathology, and low Th2/Th1 cytokine ratios in lungs post-RSV challenge (FIGS. 3 and 6).

In a newly developed SPR-based real-time kinetics assay, inhibition of interaction between recombinant CXC3R1 protein and glycosylated RSV-G protein was demonstrated with sera from rabbits vaccinated with the G ectodomains, sub-domains, and linear peptides (FIG. 7). The percentage of inhibition ranged between high (70-90%) for REG (67-298) REG ΔCCD, and G 169-207 peptide, medium (48-50%) for REG C-terminus domain (187-298) and G 148-178 peptide, or low (<30%) for all other peptides. Surprisingly, G peptide (aa 169-207) spanning the cysteine noose and the conserved CCD motif, which was the immunodominant region recognized by post-RSV infection plasma from humans across multiple age groups (Fuentes et al., PLoS Pathog. 2016; 12(4):e1005554), was not very protective in the current example (only 40% protection with large intragroup variability) (FIGS. 5D and 5F and FIG. 7B). Interestingly, animals vaccinated with this peptide showed an increase in perivasculitis score and higher levels of eotaxin in lung extracts on day 5 post viral challenge (FIGS. 6A and 6G). It was earlier reported that atypical eosinophilia in RSV infected BALB/c mice was triggered by vaccination with G peptide (aa 184-198) in a CD4-dependent mechanism (Tebbey et al., J Exp Med. 1998; 188 (10):1967-72). Another study using recombinant vaccinia virus (rVV) expressing G inserts identified residues 193-205 to be responsible for G-induced weight loss and lung eosinophilia in mice (Sparer et al., J Exp Med. 1998; 187(11):1921-6). Both sequences are included in our G (169-207) peptide that was recognized by convalescent sera from infected children. Therefore, it is possible that this immunogen has the potential to induce both protective antibodies inhibiting interaction of RSV-G with the CX3CR1 and to promote proinflammatory environment in the form of high eotaxin secretion and eosinophilia. The role of CD4 T cells will need further investigation and may vary between mice and humans.

Taken together, these data suggest that in addition to the highly conserved CCD region, other antigenic sites in the G protein may contribute to protection against RSV in animal models and possibly humans (Anderson et al., J Virol. 1988; 62(11):4232-8). It is likely that antibodies elicited by some of the G domains and linear peptides would block RSV infection in vivo by directly blocking the G protein-CX3CR1 receptor interaction on lung broncho-epithelial cells. In addition, antibodies to other regions of RSV-G could mediate protection by other effector mechanisms including antibody dependent cellular cytotoxicity (ADCC) and antibody-dependent cellular phagocytosis (ADCP) that could contribute to removal of RSV infected cells in vivo (Cortjens et al., J Virol. 2017; 91(10)). Cell mediated immunity by RSV-G specific CD8+T cells may also contribute. However G protein lacks MHC class I-restricted epitopes and has not been shown to elicit CTL responses in mice or humans (Nicholas et al., J Virol. 1990; 64(9):4232-41; Heidema et al., J Gen Virol. 2004; 85(Pt 8):2365-74). Notably, the REG ΔCCD construct elicited a favorable ratio of Th1/Th2 cytokines, different from the formalin inactivated killed RSV vaccine that skewed the immune system towards Th2 responses and showed enhanced disease in naive humans and animals after virus exposure.

Materials and Methods

Cell, viruses, and plasmids. A549 cells (Cat. No. #CCL-185) were obtained from the American Type Culture Collection (ATCC, Manassas, Va., USA) and were maintained in F-12K medium supplemented with 10% fetal bovine serum, 1X penicillin streptomycin (P-S), and L-glutamine Cells were maintained in an incubator at 37° C. under 5% $CO_2$. RSV rA2-Line19F-Firefly Luciferase (rRSV-A2-L19-FFL) expressing the firefly luciferase gene upstream of the NS1 gene was prepared by infecting sub confluent A549 cell monolayers in F-12K medium supplemented with 2% FBS and 1× Penicillin-Streptomycin (infection medium) (Fuentes et al., Vaccine. 2017; 35(4):694-702). To generate a challenge stock, at 5 days post infection (dpi), cells were freeze-thawed twice and virus was collected. Harvested viruses were cleared of cell debris by centrifugation at 3,795 g for 15 min. Virus stocks used in challenge studies were pelleted by centrifugation at 10,509 g overnight. Pelleted virus was resuspended in TEN buffer and purified by sucrose-gradient ultracentrifugation. Virus titers were determined by plaque assay on A549 cells. The optimal challenge dose ($10^6$ PFU intranasally) was determined in earlier study in which viral loads were measured by traditional plaque assay, by qRT-PCR and by live imaging (flux) and gave comparable results in terms of viral kinetics and peak values (Fuentes et al., Vaccine. 2017; 35(4):694-702). Codon-optimized RSV G coding DNA for E. coli was chemically synthesized. NotI and PacI restriction sites were used for cloning the RSV A2 G ectodomain coding sequence (amino acids 67 to 298) into the T7-based pSK expression vector for bacterial expression. DNA coding REG 67-163 and REG 187-298 were amplified by PCR using primers containing Nod and Pad restriction sites. DNA coding REG ΔCCD with residues 172-186 deleted and replaced with a $(G4S)_2$ linker was prepared by a two-step overlapping PCR. The deleted sequence contains the cysteine noose in addition to the CX3CR1 binding motif present in all RSV G proteins. All amplified DNA was digested with NotI and PacU and ligated into the T7-based pSK expression vector for bacterial expression.

Production of recombinant E. coli expressed G (REG) proteins. Recombinant RSV G 67-298 (REG 67-298), REG 67-163, REG 187-298, and REG ΔCCD proteins were expressed in E. coli BL21(DE3) cells (Novagen) and were purified as described previously (Fuentes et al., J Virol. 2015; 89(16):8193-205; Fuentes et al., Sci Rep. 2017; 7:42428). Briefly, REG proteins expressed and localized in E. coli inclusion bodies (IB) were isolated by cell lysis, denatured and renatured in redox folding buffer followed by dialysis. The dialysate was purified through a HisTrap FF chromatography column (GE Healthcare). The protein concentrations were analyzed by bicinchoninic acid (BCA) assay (Pierce), and the purity of the recombinant G proteins from E. coli (REG) was determined by SDS-PAGE. Linear peptides were synthesized chemically using Fmoc chemistry, purified by HPLC, conjugated to KLH, and dialyzed.

Production of recombinant glycosylated G protein using 293 Flp-In cells (RMG). The 293-Flp-In cell line (Cat. No. #R75007; ThermoFisher Scientific) stably expressing the RSV A2 G protein with secretory signal peptide from IgG kappa chain was developed as described previously (Fuentes et al., Vaccine. 2017; 35(4):694-702). Briefly, 293-Hp-in cells were co-transfected with the plasmids expressing Hp-in recombinase and the RSV A2 G ectodomain in DMEM media (Invitrogen). Twenty-four hours after transfection, culture medium was replaced with fresh DMEM containing 150 µg/mL of hygromycin for selection of stably transfected cells. For protein expression, cells were maintained in 293-Expression media (Invitrogen), and culture supernatant was collected every 3-4 days. Supernatant was cleared by centrifugation and filtered through a 0.45 µm filter before purification through a His-Trap FF column (GE healthcare).

Gel filtration chromatography. Proteins at a concentration of 2 mg/mL were analyzed on a Superdex 200 Increase 10/300 GL column (GE Healthcare) pre-equilibrated with phosphate-buffered saline (PBS), and protein elution was monitored at 280 nm. Protein molecular weight (MW) marker standards (GE Healthcare) were used for column calibration and for the generation of standard curves to identify the molecular weights of each purified protein.

Plaque reduction neutralization test (PRNT). For the PRNT, heat-inactivated serum was diluted 4-fold and incubated with RSV-A2 virus (diluted to yield 20-50 plaques/well) containing 10% guinea pig complement (Rockland Immunochemical; Philadelphia, Pa., USA) and incubated for 1 h at 37° C. After incubation, 100 µL of the antibody-virus mixtures were inoculated in duplicate onto A549 monolayers in 48-well plates and incubated for 1 h at 37° C. Inoculum was removed prior to adding infection medium containing 0.8% methylcellulose. Plates were incubated for 5 to 7 days at which time the overlay medium was removed and cell monolayers fixed with 100% methanol; plaques were detected by immunostaining with rabbit RSV polyclonal anti-F sera (Capella et al., J Infect Dis. 2017; 216

(11):1398-406), followed by addition of alkaline phosphatase goat anti-rabbit IgG (H +L) (Jackson) antibody. The reactions were developed by using Vector Black Alkaline Phosphatase (AP) substrate kit (Vector Labs, Burlingame, Calif.). Numbers of plaques were counted per well and the neutralization titers were calculated by adding a trend line to the neutralization curves and using the following formula to calculate 50% endpoints: antilog of [(50+y-intercept)/slope].

Rabbit immunizations. Female New Zealand white rabbits (KBL(NZW)BR strain from Charles River Labs) were immunized three times intramuscularly (i.m.) with 100 µg of each purified REG protein combined with Emulsigen adjuvant, or with KLH-conjugated RSV-G peptides combined with Emulsigen, every 28 days. Blood was collected 8 days after each immunization.

Murine immunization, RSV challenge, and sample collection. Four-to 6-week-old female BALB/c mice (BALB/cAnNCr strain code #555) were obtained from the Charles River Labs. Mice [N=6-8 per group] were immunized intramuscularly (i.m.) at day 0 and day 20 with 20 µg of purified REG protein or with 25 µg of KLH-conjugated peptides combined with Emulsigen adjuvant at total volume of 100 µL. Blood was collected from the tail vein on days 0, 14, and 30. On day 34, mice were anesthetized with isofluorane through inhalation according to mouse body weight and infected intranasally (i.n.) with $10^6$ PFU of rRSV-A2-L19-FFL as previously described (Fuentes et al., Vaccine. 2017; 35(4):694-702). Mice were sacrificed by $CO_2$ asphyxiation 5 days post-RSV challenge (previously determined to be the day with peak viral load), and blood and lungs were collected. For determination of the viral load and cytokine analysis, the left lobe of the lung was collected.

In vivo imaging of RSV-infected mice. Whole body live imaging of infected mice was performed using IVIS imaging system as previously described (Fuentes et al., Vaccine. 2017; 35(4):694-702). In brief, mice were anesthetized in an oxygen-rich induction chamber with 2% isoflurane and administered 20 µL of RediJect D-Luciferin bioluminescent substrate (Perkin Elmer) intranasally. After a 5-min interval, mice were placed in the IVIS 200 Imaging systems (Xenocorp) equipped with the Living Image software (version 4.3.1.). Bioluminescence signals were recorded for 2 min for whole body and for 1 min for lungs and nasal cavities, respectively. Images were analyzed with the LivingImage 4.5 software (PerkinElmer) according to manufacturer's instructions.

Determination of viral loads in lungs. Lungs (unperfused) were weighed and homogenized in F-12K-2% FBS-1X P-S (5 mL medium/g of lung) using an Omni (Kennesaw, Ga.) tissue homogenizer. The supernatant was cleared by centrifugation at 3,795×g for 10 min and was used immediately for viral titration by plaque assay in A549 cells as described above.

Measurement of cytokine levels in lungs. All lungs were weighed and homogenized in 5 mL of medium/g of lung, as described above, to normalize the amount of lung tissue used per sample. Homogenized lungs were further diluted in infection culture medium containing a 2× concentration of Complete EDTA Free protease inhibitor cocktail (Roche, Basel, Switzerland) and were used in a Bio-Plex Pro mouse cytokine 23-plex assay according to the manufacturer's recommendations. Plates were read using a Bio-Plex 200 system (Bio-Rad, Hercules, Calif.).

RSV ELISA. Immulon 2 HB 96-well microtiter plates were coated with 100 µL of purified RSV rA2-Line19F-FFL or RSV B1 virus in PBS ($10^4$ pfu/well) per well at 4EC overnight. After blocking with PBST containing 2% BSA, serial dilutions of mouse serum in blocking solution were added to each well, incubated for 1 h at RT, followed by addition of 2,000-fold dilution of HRP-conjugated goat anti-mouse IgG-Fc antibody, and developed by 100 µL of OPD substrate solution. Absorbance was measured at 490 nm.

Surface plasmon resonance (SPR). Steady-state equilibrium binding of post-vaccination animal sera was monitored at 25EC using a ProteOn surface plasmon resonance (SPR) biosensor (Bio-Rad). The recombinant G protein from 293T cells (RMG) was coupled to a GLC sensor chip via amine coupling with 500 resonance units (RU) in the test flow channels. Samples of 100 µL of freshly prepared sera at a 10-fold dilution or MAbs (starting at 1 µg/mL) were injected at a flow rate of 50 µL/min (contact duration, 120 seconds) for association. Disassociation was performed over a 600 seconds interval. Responses from the protein surface were corrected for the response from a mock surface and for responses from a buffer-only injection. Pre-vaccination animal sera were used as a negative control. Total antibody binding and data analysis results were calculated with Bio-Rad ProteOn Manager software (version 3.0.1).

SPR based CX3CR1 binding and inhibition assay. The recombinant G protein from 293T cells (RMG) was captured on a HTG sensor chip via Histidine tag with 500 resonance units (RU) in the test flow channels. Samples of 500 µL of freshly prepared post-2nd immunization rabbit sera at a 10-fold dilution were injected at a flow rate of 50 µL/min (contact duration, 300 seconds) for association. Following antibody binding, recombinant CX3CR1 (Abnova; 5 µg/mL) was injected at a flow rate of 50 µL/min (contact duration, 120 seconds) for association. Responses from the protein surface were corrected for the response from a mock surface and for responses from a buffer-only injection. Pre-vaccination animal sera were used as a negative control. Total CX3CR1 binding and data analysis and % inhibition by immune sera were calculated with Bio-Rad ProteOn Manager software (version 3.0.1).

Statistical analysis. The statistical significances of group differences were determined using one-way analysis of variance (ANOVA) and a Bonferroni multiple-comparison test. Correlations were calculated with a Spearman two-tailed test. P values less than 0.05 were considered significant with a 95% confidence interval.

It will be apparent that the precise details of the methods or compositions described may be varied or modified without departing from the spirit of the described embodiments. We claim all such modifications and variations that fall within the scope and spirit of the claims below.

I claim:

1. A recombinant respiratory syncytial virus (RSV) G ectodomain comprising:
   a deletion of RSV G residues 1-66 and 172-186 with residues 171 and 187 directly linked by a peptide bond, or indirectly linked by a peptide linker;
   wherein the recombinant RSV G ectodomain does not include a transmembrane domain or cytosolic tail; and
   wherein the amino acid positions correspond to SEQ ID NO: 1.

2. The recombinant RSV G ectodomain of claim 1, wherein the recombinant RSV G ectodomain comprises RSV G residues 67-171 and 187-298.

3. The recombinant RSV G ectodomain of claim 1, wherein residues 171 and 187 are linked by the peptide linker.

4. The recombinant RSV G ectodomain of claim 1, wherein the peptide linker is a glycine-serine linker.

5. The recombinant RSV G ectodomain of claim 4, wherein the peptide linker comprises the amino acid sequence set forth as GGGGSGGGGS (SEQ ID NO: 5).

6. The recombinant RSV G ectodomain of claim 1, wherein the recombinant RSV G ectodomain is a bovine RSV G ectodomain, a human subtype A RSV G ectodomain, or a human subtype B RSV G ectodomain, containing the deletion of residues 172-186 with residues 171 and 187 linked by the peptide linker.

7. The recombinant RSV G ectodomain of claim 1, comprising an amino acid sequence at least 90% identical to SEQ ID NO: 2 or SEQ ID NO: 11.

8. The recombinant RSV G ectodomain of claim 1, comprising the amino acid sequence set forth as SEQ ID NO: 2 or SEQ ID NO: 11.

9. The recombinant RSV G ectodomain of claim 1, consisting of the amino acid sequence set forth as SEQ ID NO: 2 or SEQ ID NO: 11.

10. The recombinant RSV G ectodomain of claim 1, wherein the RSV G ectodomain is not glycosylated.

11. The recombinant RSV G ectodomain of claim 1, wherein the RSV G ectodomain is soluble.

12. The recombinant RSV G ectodomain of claim 1, linked to a carrier.

13. The recombinant RSV G ectodomain of claim 1, wherein the recombinant RSV G ectodomain elicits an immune response to RSV G when administered to a subject.

14. A virus-like particle comprising the recombinant RSV G ectodomain of claim 1.

15. An isolated nucleic acid molecule encoding the recombinant RSV G ectodomain of claim 1.

16. The nucleic acid molecule of claim 15, operably linked to a promoter.

17. The nucleic acid molecule of claim 15, wherein the nucleic acid molecule is an RNA molecule.

18. An expression vector comprising the nucleic acid molecule of claim 15.

19. A viral vector comprising the nucleic acid molecule of claim 15.

20. An immunogenic composition comprising the recombinant RSV G ectodomain of claim 1, a virus like particle comprising the recombinant RSV G ectodomain, a nucleic acid molecule encoding recombinant RSV G ectodomain, an expression vector comprising the nucleic acid molecule, or a viral vector comprising the nucleic acid molecule.

21. The immunogenic comprising of claim 20, further comprising an RSV F protein, nucleic acid molecule encoding an RSV F protein, an expression vector or viral vector comprising the nucleic acid molecule encoding the RSV F protein.

22. A method of inducing an immune response to RSV G protein in a subject, comprising administering to the subject an effective amount of the recombinant RSV G ectodomain of claim 1, a virus like particle comprising the recombinant RSV G ectodomain, a nucleic acid molecule encoding the recombinant RSV G ectodomain, an expression vector comprising the nucleic acid molecule, or a viral vector comprising the nucleic acid molecule to generate the immune response.

23. The method of claim 22, wherein the immune response inhibits an RSV infection and/or reduces severity of subsequent RSV infection in the lower respiratory tract of the subject.

24. A method of detecting an antibody that specifically binds to RSV G protein, comprising contacting a sample containing antibodies with the recombinant RSV G ectodomain of claim 1 under conditions sufficient to form an immune complex, and detecting the immune complex.

25. A recombinant respiratory syncytial virus (RSV) G ectodomain comprising:
   a deletion of RSV G residues 172-186 with residues 171 and 187 indirectly linked by a peptide linker, linked to an N-terminal RSV G transmembrane domain and cytosolic tail;
   wherein the recombinant RSV G ectodomain linked to the N-terminal RSV G transmembrane domain and cytosolic tail comprises an amino acid sequence at least 90% identical to SEQ ID NO: 6 or SEQ ID NO: 15, wherein the amino acid positions correspond to SEQ ID NO: 1.

26. The recombinant RSV G ectodomain of claim 25, wherein the recombinant RSV G ectodomain linked to the N-terminal RSV G transmembrane domain and cytosolic tail comprises the amino acid sequence set forth as SEQ ID NO: 6 or SEQ ID NO: 15.

27. The recombinant RSV G ectodomain of claim 25, wherein the RSV G ectodomain is not glycosylated.

28. A virus-like particle comprising the recombinant RSV G ectodomain of claim 25.

\* \* \* \* \*